(12) United States Patent
Sun

(10) Patent No.: US 8,071,602 B2
(45) Date of Patent: Dec. 6, 2011

(54) PIPERIDINE AND PIPERAZINE DERIVATIVES

(75) Inventor: Connie L. Sun, Palo Alto, CA (US)

(73) Assignee: M's Science Corporation, Minatojima-minamimachi, Chuo-ku, Kobe (JP)

(*) Notice: Subject to any disclaimer, the term of this patent is extended or adjusted under 35 U.S.C. 154(b) by 140 days.

(21) Appl. No.: 11/992,263

(22) PCT Filed: Oct. 10, 2006

(86) PCT No.: PCT/US2006/036339
§ 371 (c)(1),
(2), (4) Date: Mar. 19, 2008

(65) Prior Publication Data
US 2010/0256162 A1    Oct. 7, 2010

Related U.S. Application Data

(60) Provisional application No. 60/720,064, filed on Sep. 23, 2005.

(51) Int. Cl.
| | |
|---|---|
| *A61K 31/497* | (2006.01) |
| *A61K 31/445* | (2006.01) |
| *C07D 401/12* | (2006.01) |
| *C07D 403/12* | (2006.01) |
| *C07D 211/68* | (2006.01) |
| *C07D 211/40* | (2006.01) |

(52) U.S. Cl. ............. 514/253.07; 514/254.09; 514/317; 514/318; 544/363; 544/373; 546/193; 546/216

(58) Field of Classification Search ............ 514/253.07, 514/254.09, 317, 318; 544/363, 373; 546/193, 546/216
See application file for complete search history.

(56) References Cited

U.S. PATENT DOCUMENTS

| | | | | |
|---|---|---|---|---|
| 2003/0130287 A1* | 7/2003 | Ackermann et al. | ..... | 514/253.07 |
| 2009/0221607 A1* | 9/2009 | Sun et al. | ..... | 514/255.01 |
| 2010/0137334 A1* | 6/2010 | Sun et al. | ..... | 514/254.11 |

* cited by examiner

*Primary Examiner* — James O Wilson
*Assistant Examiner* — Ebenezer O Sackey
(74) *Attorney, Agent, or Firm* — Paul N. King

(57) ABSTRACT

Compounds of general formula (I)

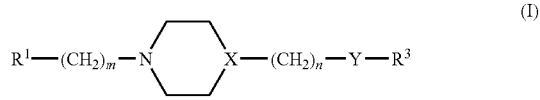

in which $R^1$, m, X, n, Y and $R^3$ have any of the meanings given in the specification, have affinity for sigma receptors and are useful in the treatment of disorders of the central nervous system.

25 Claims, No Drawings

PIPERIDINE AND PIPERAZINE DERIVATIVES

This application claims priority based on U.S. provisional application No. 60/720,064 filed Sep. 23, 2005, entitled "Piperidine and piperazine Derivatives," which is hereby incorporated herein by reference in the entirety of its disclosure.

BACKGROUND

The present invention relates to novel 1,4-piperidine and piperazine derivatives, to processes for preparing the novel derivatives, to novel intermediates useful in the process, to pharmaceutical compositions comprising the derivatives, and to the use of derivatives in the treatment of disorders of the central nervous system.

It has been disclosed in the scientific literature that certain disorders of the central nervous system may be treated using a modulator of sigma receptor function. Amongst compounds known to possess affinity for sigma ligands are certain piperidine and piperazine derivatives.

WO 91/09594 discloses compounds having affinity for sigma receptors, certain of which are piperidine or piperazine derivatives, and discloses that they are useful in the treatment of schizophrenia and other psychoses.

U.S. Pat. No. 5,736,546 discloses certain 1,4-(diphenylalkyl)piperazines having one phenyl group unsubstituted and the other phenyl group substituted by two alkoxy groups. One of the compounds disclosed is 1-[2-(3,4-dimethoxyphenyl)ethyl]-4-(3-phenylpropyl)piperazine. It is also referred to in the scientific literature as SA 4503. The compounds of U.S. Pat. No. 5,736,546 are said to be useful in the treatment of dementia, depression, schizophrenia, anxiety neurosis, diseases accompanying abnormal immune response, cryptorrhea and digestive ulcer.

WO 2004/110387 discloses that sigma ligands, in particular SA 4503, are also useful in the treatment of patients to facilitate neuronal regeneration after onset of a neurodegenerative disease, such as ischemic stroke, traumatic brain injury or spinal chord injury.

U.S. Pat. No. 5,389,630 discloses certain diamine compounds having cerebral protective action. The compound of Example 50 is a piperazine derivative, but the vast majority of the exemplified compounds are homopiperazine derivatives. The mechanism of action of the compounds is not discussed.

It has now been found that certain novel 1,4-piperidine and piperazine derivatives have high affinity for sigma receptors, in particular sigma-1 receptors.

According to one aspect, the present invention provides a compound of general formula (I)

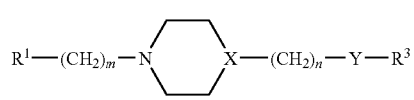

in which:—

R$^1$ represents a phenyl group that is unsubstituted or substituted by one, two or three substituents selected independently from (1-2C)alkylenedioxy, a halogen atom, a hydroxyl group, a (1-4C) alkyl group, a (3-6C)cycloalkyl group, a halo(1-4C) alkyl group, a (1-4C)alkoxy group, a cyano group, and a halo(1-4C)alkoxy group;

m is 2, 3, 4 or 5;

X is CH or N;

n is 0, 1, 2, 3, 4 or 5, provided that when X is N, n is 2, 3, 4 or 5;

Y is O, NR$^2$ or S;

R$^2$ is hydrogen, (1-4C)alkyl or phenyl(1-4C)alkyl, or is as defined for R$^3$; and R$^3$ represents indan-1-yl, indan-2-yl, 1,2,3,4-tetrahydronaphth-1-yl or 1,2,3,4-tetrahydronaphth-2-yl, each of which may bear a hydroxyl substituent on a non-aromatic carbon atom; (3-6C) cycloalkyl; or a phenyl group that is unsubstituted or substituted by one, two or three substituents selected independently from (1-2C)alkylenedioxy, a halogen atom, a hydroxyl group, a (1-4C) alkyl group, a (3-6C)cycloalkyl group, a cyano group; a phenyl group, an imidazolyl group, a halo(1-4C) alkyl group, a (1-4C)alkoxy group and a halo(1-4C)alkoxy group;

or a pharmaceutically acceptable salt thereof.

Compounds according to the invention have been found to have high affinity for sigma receptors, in particular sigma-1 receptors.

As used herein, unless otherwise indicated, the term halogen atom includes fluorine, chlorine and bromine.

The term (1-2C)alkylenedioxy includes methylenedioxy and ethylenedioxy.

An example of a (1-4C) alkyl group is methyl. Other examples are ethyl, propyl, 2-propyl, butyl, 2-butyl and t-butyl.

The term halo(1-4C)alkyl as used herein includes perfluoro(1-4C)alkyl, such as trifluoromethyl.

An example of a (1-4C)alkoxy group is methoxy. Other examples are ethoxy, propoxy and 2-propoxy.

The term halo(1-4C)alkoxy as used herein includes perfluoro(1-4C)alkoxy, such as trifluoromethoxy.

Examples of a (3-6C) cycloalkyl group are cyclopentyl and cyclohexyl.

Referring to formula (I), examples of particular values for R$^1$ are phenyl, benzo[1,3]dioxol-5-yl, 2-fluorophenyl, 3-fluorophenyl, 4-fluorophenyl, 3,4-difluorophenyl, 3-chlorophenyl, 3-methylphenyl, 2-trifluoromethylphenyl, 3-trifluoromethylphenyl, 4-trifluoromethylphenyl, 2-methoxyphenyl, 3-methoxyphenyl, 4-methoxyphenyl, 4-isopropoxyphenyl, 3,4-dimethoxyphenyl, 2,3,4-trimethoxyphenyl, 3,4,5-trimethoxyphenyl, 2-fluoro-3,4-dimethoxyphenyl, 3-chloro-4-methoxyphenyl, 4-chloro-3-methoxyphenyl, 2-trifluoromethoxyphenyl, 4-trifluoromethoxyphenyl and 3-trifluoromethoxyphenyl.

Particular examples of values for R$^1$ are phenyl, benzo[1,3]dioxol-5-yl, 2-fluorophenyl, 3,4-difluorophenyl, 2-trifluoromethylphenyl, 3-trifluoromethylphenyl, 4-trifluoromethylphenyl, 2-methoxypheny, 3-methoxyphenyl, 4-methoxyphenyl, 3,4-dimethoxyphenyl and 2-trifluoromethoxyphenyl.

Particular mention is made of compounds of formula (I) in which R$^1$ represents 3,4-dimethoxyphenyl, 4-methoxyphenyl, 4-isopropoxyphenyl, 4-trifluoromethoxyphenyl, or 3,4,5-trimethoxyphenyl.

Examples of values for m are 2 and 3. An example of a particular value for m is 2.

Examples of particular values for n are 2 and 3. An example of a particular value for n is 2.

An example of a particular value for R$^2$ is hydrogen.

Examples of particular values for Y are O and NH.

Examples of particular values for R$^3$ are phenyl, benzo[1,3]dioxol-5-yl, 2-fluorophenyl, 4-fluorophenyl, 2,4-difluorophenyl, 4-trifluoromethoxyphenyl, 2-chlorophenyl, 4-chlorophenyl, 3,4-dichlorophenyl, 4-methylphenyl, 4-isopropylphenyl, 4-t-butylphenyl, 4-cyanophenyl, 2-trifluoromethylphenyl, 4-trifluoromethylphenyl, 2-methoxyphenyl, 4-methoxyphenyl, 4-biphenyl, 4-(1-imidazolyl)phenyl, 2-fluoro-4-methoxyphenyl, 3-fluoro-4-methoxyphenyl, 3-chloro-4-methoxyphenyl, 2-trifluoromethoxyphenyl, 3,4,5-trimethoxyphenyl, and 4-trifluoromethoxyphenyl.

Particular examples for $R^3$ are phenyl, 2-fluorophenyl, 4-fluorophenyl, 2-chlorophenyl, 4-chlorophenyl, 4-methylphenyl, 4-isopropylphenyl, 4-cyanophenyl, 3,4,5-trimethoxy group, and 2-trifluoromethylphenyl.

Particular mention is made of compounds of formula (I) in which $R^3$ represents a 4-fluorophenyl group.

It will be appreciated that certain compounds of formula (I) contain a centre of asymmetry. These compounds may therefore exist and be isolated in the form of stereoisomers. The present invention provides a compound of formula (I) in any stereoisomeric form.

It will also be appreciated that the compounds of formula (I) or their pharmaceutically acceptable salts may be isolated in the form of a solvate, and accordingly that any such solvate is included within the scope of the present invention.

Certain compounds of formula (I) have also been found to possess good selectivity for sigma-1 receptors as compared with sigma-2 receptors. This selectivity for sigma-1 receptors is particularly desirable, because selectivity for sigma-2 receptors can have undesired results. For example, sigma-2 receptors have been shown to play an important role in the sigma receptor-mediated neck dystonia in rats (Matsumoto R R, et al., Pharmacol. Biochem. Behav. 36, 151-155, 1996). For example microinjection of DTG (1,3-di-2-tolyl-guanidine, a sigma-1 and sigma-2 receptor agonist) induced neck dystonia in rats while injection of SA-4503 (a selective sigma-1 agonist) had no effect (Nakazawa M et al., Pharmacol biochem. Behav., 62, 123-126, 1999). In addition sigma-2 receptors have been implicated in the regulation of cell proliferation. Cytotoxic effects have been correlated with sigma-2 receptor ligands (Vilner and Bowen, Eur. J. Pharmacol Mol Pharmacol Sect 244, 199-201, 1993). Sigma-2 selective drugs can inhibit tumor cell proliferation through mechanisms that may involve apoptosis and intracellular calcium release (Aydar E et al., Cancer Research 64, 5029-5035, 2004). Compounds of formula (I) possessing good selectivity for sigma-1 receptors are therefore particularly preferred.

According to another aspect, therefore, the present invention provides a compound which is selected from
1-(3,4-Dimethoxyphenethyl)-4-(2-(4-fluorophenoxy)ethyl) piperidine;
1-(4-(Trifluoromethyl)phenethyl)-4-(2-phenoxyethyl)piperidine;
4-(2-(2-Fluorophenoxy)ethyl)-1-(3,4-dimethoxyphenethyl) piperidine;
1-(3,4-Dimethoxyphenethyl)-4-(2-phenoxyethyl)piperazine;
1-(3-Methoxyphenethyl)-4-(2-phenoxyethyl)piperazine;
1-(4-Methoxyphenethyl)-4-(2-phenoxyethyl)piperazine;
1-(2-(Benzo[d][1,3]dioxol-5-yl)ethyl)-4-(2-phenoxyethyl) piperazine;
1-(3,4-Difluorophenethyl)-4-(2-phenoxyethyl)piperazine;
1-Phenethyl-4-(2-phenoxyethyl)piperazine;
1-(3,4-Dimethoxyphenethyl)-4-(2-(4-chlorophenoxy)ethyl) piperazine;
4-(2-(4-(3,4-Dimethoxyphenethyl)piperazin-1-yl)ethyloxy) benzonitrile;
and pharmaceutically acceptable salts thereof.

The above compounds have been found to possess good selectivity for sigma-1 over sigma-2 receptors.

The compounds of general formula (I) can be prepared by conventional processes.

According to another aspect, therefore, the present invention provides a process for preparing a compound of general formula (I), or a pharmaceutically acceptable salt thereof, which comprises
a) reducing a compound of general formula (II)

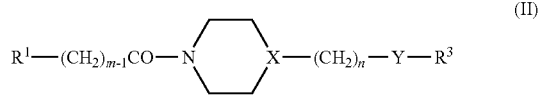

(II)

with a reducing agent;
b) for a compound of formula (I) in which X is N, reacting a compound of general formula (III)

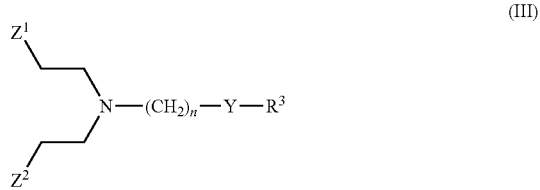

(III)

in which each of $Z^1$ and $Z^2$ independently represents a leaving atom or group, with a compound of general formula (IV)

$$R^1—(CH_2)_m—NH_2 \quad (IV)$$

or a corresponding compound in which one or two substituents on $R^1$ are protected; or
c) for a compound of formula (I) in which X is N, reacting a compound of general formula (V)

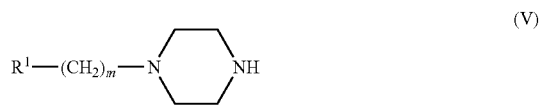

(V)

with a compound of general formula (VI)

$$Z^3—(CH_2)_n—Y—R^3 \quad (VI)$$

in which $Z^3$ represents a leaving atom or group;
followed by removing any protecting group and, optionally, forming a pharmaceutically acceptable salt.

Referring to process step a), the reducing agent can conveniently be a borane ($BH_3$), a borohydride reducing agent, such as sodium borohydride, or an alkali metal aluminium hydride, such as lithium aluminium hydride. The reduction is conveniently performed in the presence of a solvent such as an ether, for example tetrahydrofuran. The temperature at which the reduction is carried out is conveniently in the range of from −25 to 100° C., such as from −10 to 40° C.

Compounds of general formula (II) can be prepared by reacting a compound of general formula (VII)

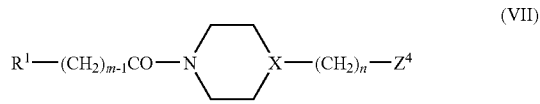

(VII)

in which $Z^4$ represents a leaving atom or group, such as a p-toluenesulfonyloxy group, with a compound of general formula (VIII)

$$H—Y—R^3 \quad (VIII)$$

Compounds of general formula (VII) can be prepared from a corresponding compound of general formula (IX),

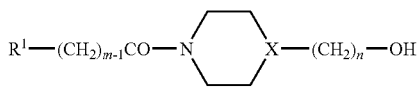
(IX)

for example by reaction with a sulfonyl halide, such as p-toluenesulfonyl chloride.

Compounds of general formula (IX) can be prepared by reacting a compound of general formula (X)

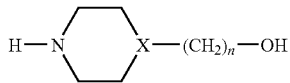
(X)

with a compound of general formula (XI)

$R^1$—$(CH_2)_{m-1}$COOH  (XI)

or a reactive derivative thereof, using standard amide bond coupling conditions.

Alternatively, compounds of general formula (II) can be prepared by reacting a compound of general formula (XII)

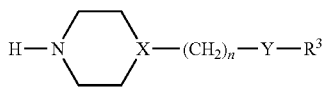
(XII)

with a compound of general formula (XI), or a reactive derivative thereof, using standard amide bond coupling conditions.

Compounds of general formula (XII) can be prepared by deprotecting a compound of general formula (XIII)

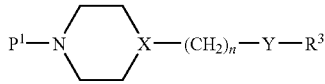
(XIII)

in which $P^1$ represents an amino protecting group, such as t-butoxycarbonyl.

Compounds of general formula (XIII) can be prepared from the corresponding compounds of general formula (XIV)

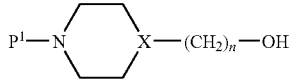
(XIV)

following the procedure for preparing a compound of general formula (II) from a compound of general formula (IX).

Referring to process step b), the leaving atoms or groups represented by $Z^1$ and $Z^2$ may be, for example, hydrocarbylsulfonyloxy groups, such as methanesulfonyloxy or p-toluenesulfonyloxy, or halogen atoms, such as chlorine atoms.

The reaction is conveniently performed at a temperature in the range of from 0 to 100° C., such as from 50 to 90° C. Convenient solvents include organic solvents, for example amides such as dimethylformamide. The reaction is conveniently performed in the presence of a base, for example an alkali metal carbonate such as potassium carbonate. The reaction may be performed in the presence of a catalyst, such as sodium iodide.

Compounds of general formula (III) can be prepared from the corresponding compounds of general formula (XV)

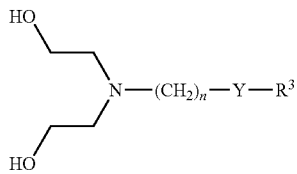
(XV)

for example by reaction with thionyl chloride to afford a compound of formula (III) in which $Z^1$ and $Z^2$ represent chlorine atoms.

Compounds of general formula (XV) can be prepared by reacting a compound of general formula (XVI)

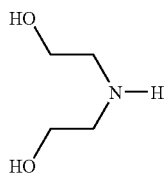
(XVI)

with a compound of general formula (XVII)

$Z^5$—$(CH_2)_n$—Y—$R^3$  (XVII)

in which $Z^5$ represents a leaving atom or group, for example a halogen atom such as a bromine atom.

Referring to process step c), the leaving atom or group represented by $Z^3$ may be, for example, a hydrocarbylsulfonyloxy group, such as p-toluenesulfonyloxy. Convenient solvents include ketones, such as acetone. The reaction is conveniently performed at a temperature in the range of from 0 to 100° C.

A pharmaceutically acceptable salt may be formed by a conventional method, such as by reacting a compound of formula (I) with a pharmaceutically acceptable acid, such as hydrochloric acid.

Certain of the intermediates, for example compounds of formula (II), may be novel. The invention also provides the entire novel intermediates disclosed herein.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of formula (I) or a pharmaceutically acceptable salt thereof, as defined hereinabove, together with a pharmaceutically acceptable diluent or carrier.

According to another aspect, the present invention provides the compound of formula (I), or a pharmaceutically acceptable salt thereof, for use in therapy.

According to another aspect, the present invention provides the use of the compound of formula (I), or a pharmaceutically acceptable salt thereof, for the manufacture of a medicament for the treatment of a disorder responsive to a modulator of sigma receptor function.

According to another aspect, the present invention provides a method of treating a condition responsive to a modulator of sigma receptor function in a patient requiring treatment, which comprises administering to said patient an effective amount of a compound of formula (I) or a pharmaceutically acceptable salt thereof.

The subject may be a human or a non-human animal, such as a non-human mammal, for example a cat, dog, horse, cow or sheep.

The disorder responsive to a sigma receptor modulator may be, for example, a disorder of the central nervous system, such as a neurological disorder or a psychiatric disorder that has been linked to sigma receptors. Examples of neurological disorders include cerebral deficits subsequent to cardiac bypass surgery and grafting, cerebral ischemia (e.g. associated with stroke or cardiac arrest); spinal cord trauma; head trauma; multiple sclerosis, Alzheimer's Disease; Huntington's Chorea; amyotrophic lateral sclerosis; AIDS-induced dementia; muscular spasms; convulsions; drug tolerance, withdrawal, and cessation (i.e. opiates, benzodiazepines, nicotine, cocaine, or ethanol); ocular damage and retinopathy; cognitive disorders; idiopathic and drug-induced Parkinson's Disease; pain; and movement disorders such as tardive dyskinesia. Examples of psychiatric disorders that are treated with a compound of formula I include schizophrenia, anxiety and related disorders (e.g. panic attack and stress-related disorders), depression, bipolar disorders, psychosis, and obsessive compulsive disorders.

The compounds according to the invention are of particular interest for use as neuroprotective agents and in the treatment of patients to facilitate neuronal regeneration and functional recovery after onset of a neurodegenerative disease, in particular ischemic stroke, traumatic brain injury, spinal cord injury, and multiple sclerosis.

The dosage of the compounds of formula (I) will depend upon the nature and severity of the condition being treated, the administration route and the size and species of the subject. In general, quantities in the range of from 0.01 to 100 mg/kg bodyweight will be administered.

As used herein, the term "treatment" includes prophylactic use. The term "effective amount" refers to the amount of the compound of formula (I) that is effective to reduce or inhibit the development of the symptoms of the disorder being treated.

The compound according to the invention may be administered alone or in combination with another therapeutic agent having a different mode of action.

The ability of a compound to bind to a sigma receptor may be demonstrated by one or more of the following tests.

Sigma-1 ($\sigma$1) and sigma-2 ($\sigma$2) receptor binding assays are carried out in membranes from HEK-293 (Human Embryonic Kidney) cells.

Membrane Preparation:

Confluent HEK-293 cells are harvested in PBS/5 mM EDTA. They are centrifuged at 2000 rpm for 5 min and then washed two times in PBS. Cells are homogenized in 20 mM Tris-HCL (pH=7.5) containing 5 mM EDTA, 0.5 mM PMSF and 0.5 µg/ml leupeptin using a Dounce homogenizer and sonicated for 5 minutes.

Nuclear debris and intact cells are removed by centrifugation at 3000 rpm for 10 minutes at 4° C. The supernatant is centrifuged at 12000 rpm for 30 minutes and the resulting pellet is resuspended in 25 mM Tris-HCL (pH=7.5), 25 mM $Mg_2Cl$, 10% sucrose containing 0.5 mM PMSF, 2 mM AEBSF, 1 mM EDTA, 130 µM bestatin, 14 µM E-64, 1 µM leupeptin and 0.3 mM aprotinin.

Proteins are determined using the Bio Rad Protein Assay Dye Reagent and the membranes are aliquoted and frozen at −80° C.

$\sigma$1 Receptor Binding Assay

The binding assays are performed in 96-well plates.

$\sigma$1 receptors are labeled using the $\sigma$1 selective probe (+)-[$^3$H] Pentazocine (Bowen W D et al, Mol Neuropharmacol 3, 117-126, 1993).

Total binding is determined by incubating 50 µg of HEK-293 cell membranes with 10 nM (+)-[$^3$H]-pentazocine (Perkin-Elmer, 35 Ci/mmol) and assay buffer (50 mM Tris-HCl, pH=8.3) in a total volume of 200 µl. Non specific binding is determined in the presence of 10 µM unlabeled pentazocine. For competition experiments, 50 µl of displacing compound is added at 8 different concentrations. Incubations are carried out for 120 min at 37° C. Assays are terminated by dilution with ice-cold 10 mM Tris-HCl, pH=8.3 and vacuum filtration through glass fibers using a Skatron cell harvester from Molecular Devices. The filters are washed three times and the membrane-bound radioactivity is determined in a Microbeta scintillation counter.

Filters are soaked in 0.5% polyethyleneimine for 1 hour before use.

Specific binding is determined by subtraction of non specific binding from total binding. $IC_{50}$ values (concentration of competing ligand required for 50% inhibition of [$^3$H]-pentazocine binding) are analyzed by non-linear regression fit using the GraphPad Prism software.

$\sigma$2 Receptor Binding Assay

The binding assays are performed in 96-well plates $\sigma$2 receptors are labeled using [$^3$H] DTG (Di-o-tolylguanidine), under conditions in which $\sigma$1 receptors are masked with the $\sigma$1 selective compound pentazocine (Hellewell S B et al, Eur. J. Pharmacol, 268, 9-18, 1994).

Total binding is determined by incubating 50 µg of HEK-293 cell membranes with 10 nM [$^3$H]-DTG (Perkin-Elmer, 58 Ci/mmol) in the presence of 10 µM pentazocine and assay buffer (50 mM Tris-HCl, pH=8.3) in a total volume of 200 µl. Non specific binding is determined in the presence of 10 µM unlabeled DTG. For competition experiments, 50 µl of displacing compound is added at 8 different concentrations. Incubations are carried out for 120 min at 37° C. Assays are terminated by dilution with ice-cold 10 mM Tris-HCl, pH=8.3 and vacuum filtration through glass fibers using a Skatron cell harvester from Molecular Devices. The filters are washed three times and the membrane-bound radioactivity is determined in a Microbeta scintillation counter.

Filters are soaked in 0.5% polyethyleneimine for 1 hour before use.

Specific binding is determined by subtraction of non specific binding from total binding. $IC_{50}$ values (concentration of competing ligand required for 50% inhibition of [³H]-DTG binding) are analyzed by non-linear regression fit using the GraphPad Prism software The compounds exemplified herein have all been found to have an $IC_{50}$ of less than 700 nM in the σ1 receptor binding assay.

The following examples illustrate the invention.

EXAMPLE 1

1-(3,4-Dimethoxyphenethyl)-4-(2-(4-chlorophenoxy)ethyl)piperidine

Step 1: 2-(3,4-Dimethoxyphenyl)-1-[4-(2-hydroxyethyl)piperidin-1-yl]ethanone (A)

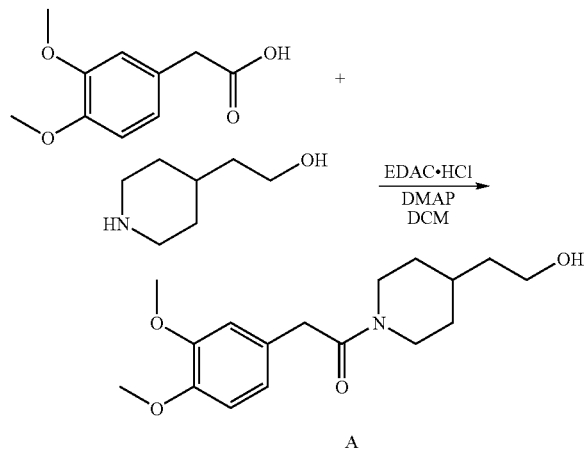

To an ice-cold solution of 3,4-dimethoxyphenylacetic acid (7.60 g, 38.7 mmol), N,N-dimethylaminopyridine (DMAP; 11.4 g, 93 mmol), and 4-piperidin-ethanol (5 g, 39 mmol) in dry dichloromethane (DCM; 80 mL) was added N-(3-dimethylaminopropyl)-N'-ethylcarbodiimide hydrochloride (EDAC.HCl; 9.65 g, 50.3 mmol) in one portion. The cooling bath was removed and the reaction was allowed to warm to room temperature. After five hours, HPLC analysis revealed the 3,4-dimethoxyphenylacetic acid was consumed. The reaction mixture was washed once with 1 N $HCl_{(aq)}$ (90 mL) and concentrated in vacuo. The residue was chromatographed to yield the title compound (A; 10.67 g, 90% yield) as viscous oil.

¹H NMR (400 MHz, CDCl₃) 0.91 (br m, 1H), 1.04 (br m, 1H), 1.44 (q, J=6.6 Hz, 2H), 1.64 (m, 3H), 1.73 (br s, 2H), 2.56 (br m, 1H), 2.92 (br m, 1H), 3.64 (m, 4H), 3.84 (s, 3H), 3.84 (s, 3H), 4.59 (br m, 1H), 6.73 (dd, J=2.0, 8.2 Hz, 1H), 6.78 (d, J=2.0 Hz, 1H), 6.79 (d, J=8.2 Hz, 1H).

m/z 308 [M+1]⁺.

Step 2: Toluene-4-sulfonic acid 2-{1-[2-(3,4-dimethoxyphenyl)-acetyl]piperidin-4-yl}-ethyl ester (B)

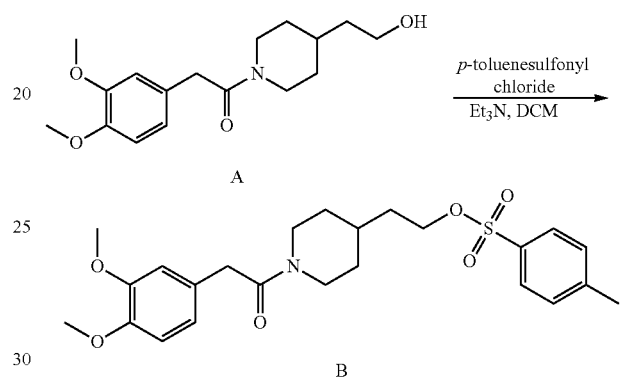

To a solution of A (10.67 g, 34.7 mmol) in dry DCM (100 mL) was added triethylamine (Et₃N, 7.5 mL, 53.8 mmol). The reaction mixture was cooled to 0° C. p-Toluenesulfonyl chloride (10.0 g, 52.4 mmol) was added in one portion, and the mixture was stirred for five minutes. The cooling bath was removed and the reaction mixture was allowed to warm to room temperature as it stirred for 12 h. TLC analysis revealed the reaction to be nearly complete. The reaction mixture was washed once with 1 N $HCl_{(aq)}$ (100 mL), concentrated in vacuo, and purified by chromatography to yield the title compound (B; 14.2 g, 88% yield) as an oil. m/z 462 [M+1]⁺.

Step 3: 1-{4-[2-(4-Chlorophenoxy)ethyl]piperidin-1-yl}-2-(3,4-dimethoxyphenyl)-ethanone (C)

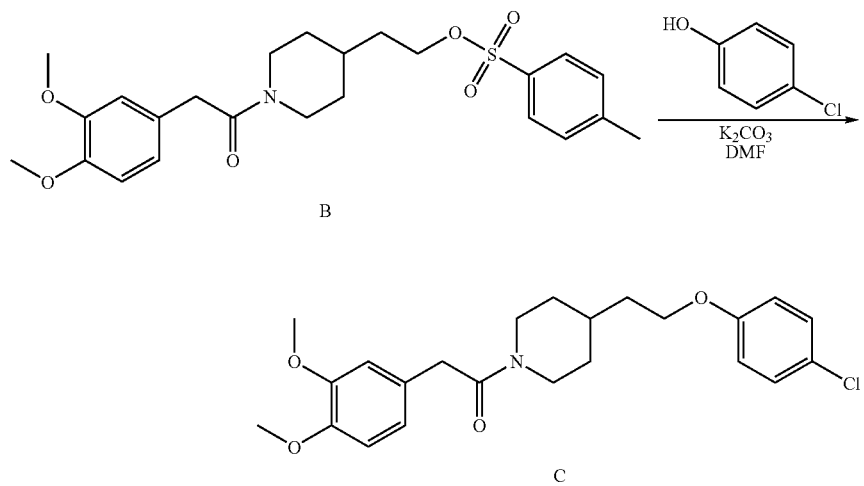

In a 20-mL reaction vessel equipped with a magnetic stir bar, B (1.4 g, 3.0 mmol), dry N,N-dimethylformamide (DMF; 11 mL), potassium carbonate (K$_2$CO$_3$; 1.26 g, 9.1 mmol) and 4-chlorophenol (0.78 g, 6.1 mmol) were heated at 75° C. for 15 h. The starting material was consumed by LC analysis. The reaction mixture was concentrated by heating under a nitrogen stream. The residue was dissolved in DCM (10 mL) and washed with water (10 mL). The organic layer was concentrated by heating under a nitrogen stream, and the residue was chromatographed to yield the title compound (C, 1.22 g, 96% yield) as an oil.

m/z 418 [M+1]$^+$.

Step 4: 1-(3,4-Dimethoxyphenethyl)-4-(2-(4-chlorophenoxy)ethyl)piperidine

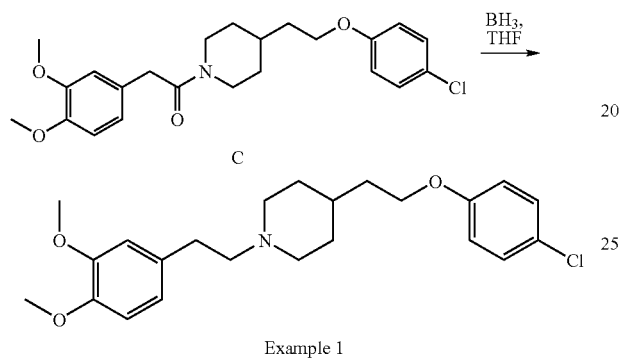

Example 1

In a 20-mL reaction vessel equipped with a magnetic stir bar, C (1.22 g, 2.9 mmol) was dissolved in dry tetrahydrofuran (THF; 6.7 mL) with stirring. The solution was cooled to 0° C., and 1.0 M borane (BH$_3$) solution in THF (8.8 mL, 8.8 mmol) was added slowly. After 10 minutes the cooling bath was removed, and the reaction mixture was stirred at room temperature for 12 h. LC analysis revealed complete consumption of C. Methanol was added slowly until gas evolution ceased (3-6 mL). The reaction mixture was concentrated by heating under a nitrogen stream. The residue was chromatographed to afford the title compound (0.17 g, 15%).

$^1$H NMR (400 MHz, DMSO-d$_6$): δ 1.5-1.9 (m, 7H), 2.6-3.0 (m, 8H), 3.71 (s, 3H), 3.74 (s, 3H), 4.01 (m, 2H), 6.75 (m, 1H), 6.81 (d, 1H), 6.88 (d, 1H), 6.96 (m, 2H), 7.30 (m, 2H).

m/z 404 [M+1]$^+$.

The following compounds were prepared using the same method as described in Example 1.

EXAMPLE 2

1-(3,4-Dimethoxyphenethyl)-4-(2-(4-fluorophenoxy)ethyl)piperidine

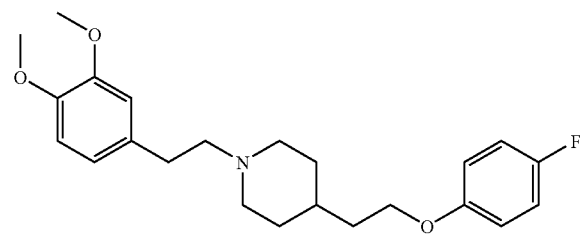

$^1$H NMR (400 MHz, DMSO-d$_6$): δ 1.47-1.7 (m, 8H), 2.7-3.1 (m, 7H), 3.72 (s, 3H), 3.75 (t, s, 3H), 3.97 (t, 2H), 6.76 (m, 1H), 6.82 (s, 1H), 6.86 (d, 1H), 6.94 (m, 2H), 7.09 (t, 2H).

m/z 388 [M+1]$^+$.

EXAMPLE 3

1-(3,4-Dimethoxyphenethyl)-4-(2-(p-tolyloxy)ethyl)piperidine

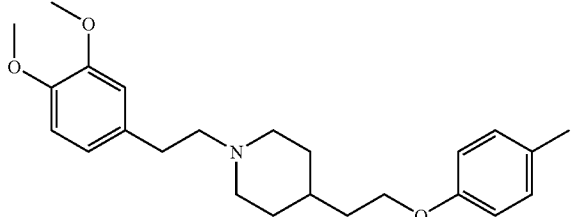

$^1$H NMR (400 MHz, CDCl$_3$): δ 1.4-1.9 (m, 7H), 2.20 (s, 3H), 2.6-3.0 (m, 8H), 3.69 (s, 3H), 3.72 (s, 3H), 3.95 (m, 2H), 6.73 (m, 1H), 6.78 (m, 3H), 6.85 (d, 1H), 7.04 (d, 2H).

m/z 384 [M+1]$^+$.

EXAMPLE 4

1-(3,4-Dimethoxyphenethyl)-4-(2-(4-isopropylphenoxy)ethyl)piperidine

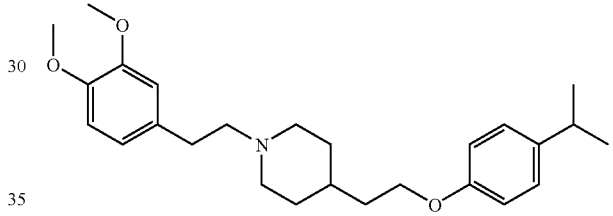

$^1$H NMR (400 MHz, DMSO-d$_6$): δ 1.13 (d, 6H), 1.5-1.9 (m, 8H), 2.6-3.0 (m, 8H), 3.69 (s, 3H), 3.73 (s, 3H), 3.94 (m, 2H), 6.72 (m, H), 4.06 (m, 2H), 6.72 (m, 1H), 6.80 (s, 1H), 6.85 (d, 1H), 6.90 (m, 1H), 6.09 (t, 1H), 7.16 (m, 2H).

m/z 388 [M+1]$^+$.

EXAMPLE 5

4-(2-(2-Fluorophenoxy)ethyl)-1-(3,4-dimethoxyphenethyl)piperidine

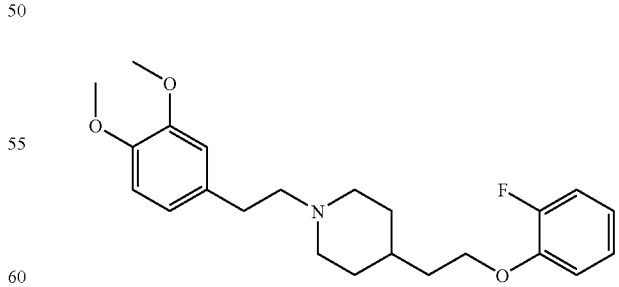

$^1$H NMR (400 MHz, CDCl$_3$): δ 1.4-1.9 (m, 8H), 2.6-3.0 (m, 7H), 3.69 (s, 3H), 3.72 (s, 3H), 4.06 (m, 2H), 6.72 (m, 1H), 6.80 (s, 1H), 6.85 (d, 1H), 6.90 (m, 1H), 6.09 (t, 1H), 7.16 (m, 2H).

m/z 388 [M+1]$^+$.

EXAMPLE 6

4-(2-(2-Chlorophenoxy)ethyl)-1-(3,4-dimethoxyphenethyl)piperidine

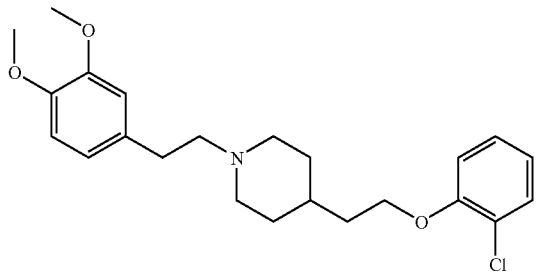

$^1$H NMR (400 MHz, DMSO-$d_6$): δ 1.54-1.89 (m, 7H), 2.58-2.66 (t, 1H), 2.80-3.03 (m, 6H), 3.71 (s, 3H), 3.74 (s, 3H), 4.09-4.13 (m, 2H), 6.72 (m, 1H), 6.82-6.90 (m, 2H), 6.93 (t, 1H), 7.12 (d, 1H), 7.27 (t, 1H), 7.38 (d, 1H).

m/z 404 [M+1]$^+$.

EXAMPLE 7

4-(2-(2-(Trifluoromethyl)phenoxy)ethyl)-1-(3,4-dimethoxyphenethyl)piperidine

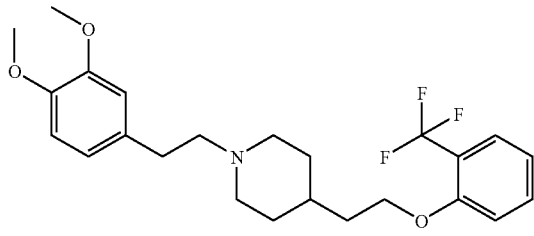

$^1$H NMR (400 MHz, CDCl$_3$): δ 1.4-1.9 (m, 8H), 2.6-3.0 (m, 7H), 3.69 (s, 3H), 3.72 (s, 3H), 4.14 (t, 2H), 6.73 (d, 1H), 6.83 (m, 2H), 7.06 (t, 1H), 7.24 (d, 1H), 7.59 (m, 2H).

m/z 438 [M+1]$^+$.

EXAMPLE 8

1-(3,4-Dimethoxyphenethyl)-4-(2-phenoxyethyl)piperidine

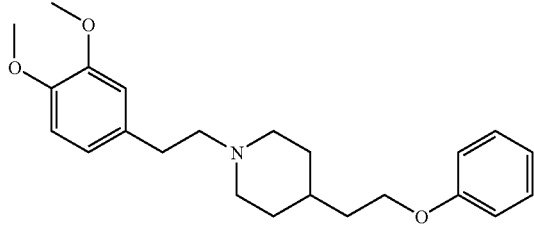

$^1$H NMR (400 MHz, DMSO-$d_6$): δ 1.4-1.9 (m, 8H), 2.6-3.0 (m, 7H), 3.69 (s, 3H), 3.72 (s, 3H), 3.99 (m, 2H), 6.71 (t, 1H), 6.80 (s, 1H), 6.84-6.92 (m, 4H), 7.26 (m, 2H).

m/z 370 [M+1]$^+$.

EXAMPLE 9

1-(2-(Benzo[d][1,3]dioxol-5-yl)ethyl)-4-(2-phenoxyethyl)piperidine

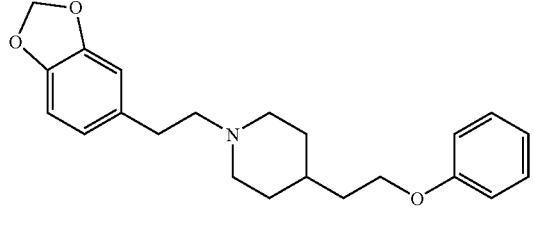

The title compound was prepared using a similar synthetic route as described in Example 1 but starting with methylenedioxyphenylacetic acid instead of 3,4-dimethoxyphenylacetic acid.

$^1$H NMR (400 MHz, CDCl$_3$): δ 1.5-1.99 (m, 8H), 2.7-3.0 (m, 7H), 3.98 (m, 2H), 5.95 (s, 2H), 6.66 (m, 1H), 6.79-6.81 (m, 2H), 6.91 (m, 3H), 7.25 (t, 2H) m/z 354 [M+1]$^+$.

The following compounds can be prepared using the same procedure as described in Example 1:

4-[2-(4-Chloro-phenoxy)ethyl]-1-[2-(3,4-dimethoxyphenyl)ethyl]piperidine 4-(2-{1-[2-(3,4-Dimethoxyphenyl)-ethyl]piperidin-4-yl}ethoxy)benzonitrile 1-[2-(3,4-Dimethoxyphenyl)ethyl]-4-[2-(4-methoxyphenoxy)ethyl]piperidine 4-[2-(Biphenyl-4-yloxy)ethyl]-1-[2-(3,4-dimethoxyphenyl)ethyl]piperidine 4-[2-(Benzo[1,3]dioxol-5-yloxy)ethyl]-1-[2-(3,4-dimethoxyphenyl)ethyl]piperidine 1-[2-(3,4-Dimethoxyphenyl)ethyl]-4-[2-(4-trifluoromethylphenoxy)ethyl]piperidine 1-[2-(3,4-Dimethoxyphenyl)ethyl]-4-[2-(4-imidazol-1-ylphenoxy)ethyl]piperidine 1-[2-(3,4-Dimethoxyphenyl)ethyl]-4-[2-(4-trifluoromethoxyphenoxy)ethyl]piperidine 1-[2-(3,4-Dimethoxyphenyl)ethyl]-4-[2-(2-methoxyphenoxy)ethyl]piperidine 1-[2-(3,4-Dimethoxyphenyl)ethyl]-4-[2-(2-trifluoromethoxyphenoxy)ethyl]piperidine 1-[2-(3,4-Dimethoxyphenyl)ethyl]-4-[2-(3-fluoro-4-methoxyphenoxy)ethyl]piperidine 4-[2-(3-Chloro-4-methoxyphenoxy)ethyl]-1-[2-(3,4-dimethoxyphenyl)ethyl]piperidine and 4-[2-(3,4-Dichlorophenoxy)ethyl]-1-[2-(3,4-dimethoxyphenyl)ethyl]piperidine.

EXAMPLE 10

N-(2-(1-(3,4-Dimethoxyphenethyl)piperidin-4-yl)ethyl)benzenamine

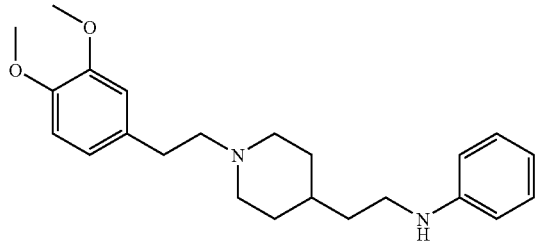

The title compound was prepared using the same procedure as described in Example 1 by replacing 4-chlorophenol with aniline in Step 3:

$^1$H NMR (400 MHz, CDCl$_3$): δ 1.4-1.9 (m, 8H), 2.6-3.0 (m, 9H), 3.69 (s, 3H), 3.72 (s, 3H), 5.35 (m, 1H), 6.47 (t, 1H), 6.51 (d, 2H), 6.73 9 (m, 1H), 6.80 (s, 1H), 6.85 (d, 1H), 7.03 (m, 2H).

m/z 369 [M+1]$^+$.

The following compounds can be prepared using the same procedure as described in Example 10:
(2-{1-[2-(3,4-Dimethoxyphenyl)ethyl]piperidin-4-yl}ethyl)-(4-fluorophenyl)amine
(4-Chlorophenyl)-(2-{1-[2-(3,4-dimethoxyphenyl)-ethyl]-piperidin-4-yl}ethyl)amine
4-(2-{1-[2-(3,4-Dimethoxyphenyl)ethyl]piperidin-4-yl}ethylamino)benzonitrile
(2-{1-[2-(3,4-Dimethoxyphenyl)ethyl]piperidin-4-yl}ethyl)-(4-methoxyphenyl)amine
Biphenyl-4-yl-(2-{1-[2-(3,4-dimethoxyphenyl)ethyl]piperidin-4-yl}ethyl)amine
Benzo[1,3]dioxol-5-yl-(2-{1-[2-(3,4-dimethoxyphenyl)ethyl]piperidin-4-yl}ethyl)amine
(2-{1-[2-(3,4-Dimethoxyphenyl)ethyl]piperidin-4-yl}ethyl)-(4-trifluoromethylphenyl)-amine
(2-{1-[2-(3,4-Dimethoxyphenyl)ethyl]piperidin-4-yl}ethyl)-p-tolylamine
(2-{1-[2-(3,4-Dimethoxyphenyl)ethyl]piperidin-4-yl}ethyl)-(4-isopropylphenyl)amine
(2-{1-[2-(3,4-Dimethoxyphenyl)ethyl]piperidin-4-yl}ethyl)-(4-imidazol-1-yl-phenyl)-amine
(2-{1-[2-(3,4-Dimethoxyphenyl)ethyl]piperidin-4-yl}ethyl)-(4-trifluoromethoxy-phenyl)amine
(2-{1-[2-(3,4-Dimethoxyphenyl)ethyl]piperidin-4-yl}ethyl)-(2-fluorophenyl)amine
(2-{1-[2-(3,4-Dimethoxyphenyl)ethyl]-piperidin-4-yl}ethyl)-(2-methoxyphenyl)amine
(2-Chloro-phenyl)-(2-{1-[2-(3,4-dimethoxyphenyl)ethyl]piperidin-4-yl}ethyl)amine
(2-{1-[2-(3,4-Dimethoxyphenyl)ethyl]-piperidin-4-yl}ethyl)-(2-trifluoromethylphenyl)-amine
(2-{1-[2-(3,4-Dimethoxy-phenyl)ethyl]-piperidin-4-yl}ethyl)-(2-trifluoromethoxy-phenyl)amine
(2-{1-[2-(3,4-Dimethoxyphenyl)ethyl]piperidin-4-yl}ethyl)-(2-fluoro-4-methoxy-phenyl)amine
(2-{1-[2-(3,4-Dimethoxy-phenyl)ethyl]piperidin-4-yl}ethyl)-(3-fluoro-4-methoxy-phenyl)amine
(3-Chloro-4-methoxyphenyl)-(2-{1-[2-(3,4-dimethoxyphenyl)ethyl]piperidin-4-yl}-ethyl)amine and
(3,4-Dichloro-phenyl)-(2-{1-[2-(3,4-dimethoxyphenyl)ethyl]piperidin-4-yl}ethyl)amine.

EXAMPLE 11

1-(2-Methoxyphenethyl)-4-(2-phenoxyethyl)piperidine

Step 1: 4-[2-(Toluene-4-sulfonyloxy)ethyl]piperidine-1-carboxylic acid tert-butyl ester (D)

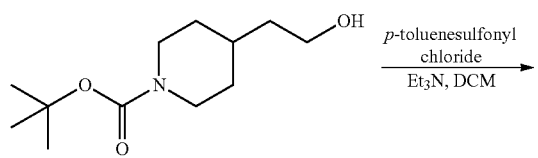

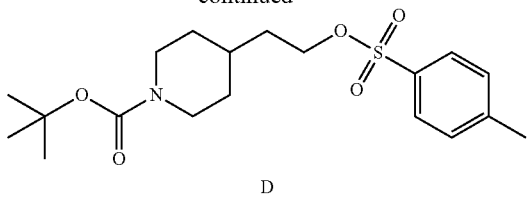

D

To an ice-cold solution of N-Boc-4-piperidine-ethanol (5.0 g, 21.8 mmol) and Et$_3$N (4.6 mL, 33.0 mmol) in dry DCM (10 mL) was added p-toluenesulfonyl chloride (6.25 g, 32.8 mmol) slowly. Upon addition, the reaction was warmed to room temperature and stirred for 20 h. The reaction mixture was washed with water (40 mL), 10% (wt/v) citric acid$_{(aq)}$ (40 mL), and saturated NaHCO$_{3(aq)}$ (40 mL). The DCM layer was dried with MgSO$_4$, filtered and concentrated in vacuo to give a pale yellow oil, which was chromatographed to give the title compound (7.47 g, 89% yield) as a clear and colorless oil.

$^1$H NMR (400 MHz, CDCl$_3$) 1.02 (m, 2H), 1.43 (s, 9H), 1.50-1.57 (m, 5H), 2.44 (s, 3H), 2.60 (br t, 2H), 4.02 (br d, 2H), 4.06 (t, 2H), 7.34 (d, 2H), 7.78 (d, 2H).

Step 2: 4-(2-Phenoxy-ethyl)-piperidine-1-carboxylic acid tert-butyl ester (E)

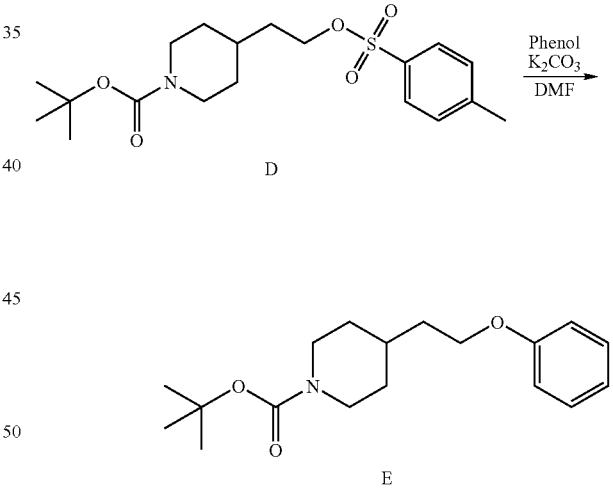

To a solution of D (8.24 g, 21.5 mmol) in dry DMF (85 mL) was added potassium carbonate (K$_2$CO$_3$; 8.9 g, 64 mmol) and phenol (4.0 g, 42.5 mmol). The reaction mixture was heated to 70-75° C. for 4 h, cooled to room temperature, and poured into water (300 mL). The mixture was extracted with ethyl acetate (3×100 mL). The ethyl acetate extracts were combined, washed with 0.25 M K$_2$CO$_{3(aq)}$ (100 mL) and saturated sodium chloride (100 mL), dried over MgSO$_4$, and concentrated in vacuo. The resultant oil was run through a silica plug to remove very polar material, thus a mixture of the title compound and phenol (7.95 g) was isolated. This material was carried on to the next step without further purification.

m/z 205 [M-CO$_2$C(CH$_3$)$_3$]$^+$.

Step 3: 4-(2-Phenoxyethyl)-piperidine, hydrochloride salt (F)

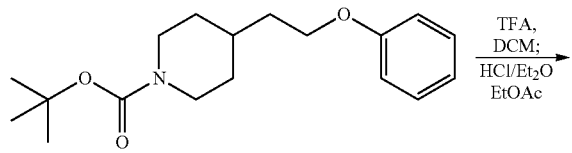

To a solution of E and phenol (7.95 g, 21.5 mmol E in theory) in DCM (80 mL) was added trifluoroacetic acid (20 mL) in a slow stream, and the mixture was stirred overnight at room temperature. The starting material was consumed by TLC analysis. The reaction mixture was washed with water (110 mL), and the aqueous phase was back-extracted with DCM (25 mL). The combined DCM layers were washed with saturated $NaHCO_{3(aq)}$ (100 mL), dried over $MgSO_4$, and concentrated to an oil (7.32 g). A portion of the oil (6.60 g) was dissolved in EtOAc (100 mL). With stirring 2 M HCl in $Et_2O$ (Aldrich; 13.5 mL) was added dropwise. The mixture was stirred for 1.5 h, filtered, washed with EtOAc, and dried in vacuo to give F (4.0 g, 85% yield) as a white solid.

$^1$H NMR (400 MHz, DMSO-$d_6$) 1.39 (m, 2H), 1.67 (q, J=6.4 Hz, 2H), 1.76 (m, 1H), 1.84 (br d, 2H), 2.83 (br q, J=11.3 Hz, 2H), 3.22 (br d, J=12.9 Hz, 2H), 4.00 (t, J=6.3 Hz, 2H), 6.90-6.93 (m, 3H), 7.28 (m, 2H), 8.73 (br s, 1H), 8.96 (br s, 1H).

Step 4: 2-(2-Methoxy-phenyl)-1-[4-(2-phenoxy-ethyl)piperidin-1-yl]ethanone (G)

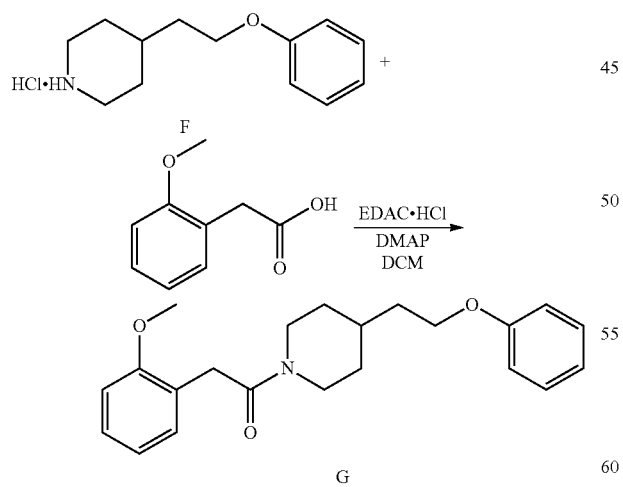

To a solution of F (0.32 g, 1.3 mmol), (2-methoxyphenyl) acetic acid (0.26 g, 1.6 mmol), and DMAP (0.55 g, 4.5 mmol) in DCM (6.5 mL) was added EDAC.HCl (0.36 g, 1.9 mmol). The reaction was stirred overnight at room temperature. HPLC analysis revealed complete consumption of F. The reaction mixture was washed with 1 N $HCl_{(aq)}$ (2×5 mL), dried over $MgSO_4$, and concentrated by heating under a nitrogen stream to afford the title compound, which was carried on to the next step without further purification. m/z 354 [M+1]$^+$.

Step 5: 1-[2-(2-Methoxyphenyl)ethyl]-4-(2-phenoxy-ethyl)piperidine hydrochloride

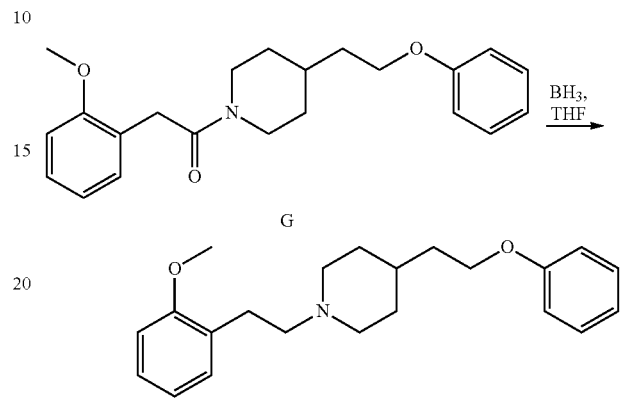

Example 11

To an ice-cold solution of crude residue G (1.3 mmol in theory) in dry THF (3 mL) was added 1.0 M $BH_3$ in THF (Aldrich; 4.1 mL, 4.1 mmol) dropwise. Upon addition, the reaction mixture was warmed to room temperature and continued stirring for 19 h. HPLC analysis revealed the complete consumption of G. Methanol was added slowly until gas evolution ceased (1-3 mL). The reaction mixture was concentrated by heating under a nitrogen stream. The residue was chromatographed to afford the title compound (0.35 g, 79% from Step 4).

$^1$H NMR (400 MHz, DMSO-$d_6$): δ 1.5-1.7 (m, 8H), 2.8-3.0 (m, 7H), 3.77 (s, 3H), 3.98 (m, 2H), 6.84-6.95 (m, 5H), 7.13-7.27 (m, 4H).

m/z 340 [M+1]$^+$.

The following compounds were prepared using the same method as described in Example 11.

EXAMPLE 12

1-(3-Methoxyphenethyl)-4-(2-phenoxyethyl)piperidine

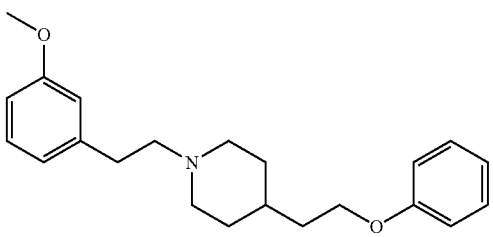

$^1$H NMR (400 MHz, $CDCl_3$): δ 1.40-1.80 (m, 7H), 2.10-2.40 (m, 1H), 2.48 (t, 1H), 2.89-3.18 (m, 6H), 3.81 (s, 3H), 4.02 (m, 2H), 6.76-6.97 (m, 6H), 7.21-7.31 (m, 3H)

m/z 340 [M+1]$^+$..

EXAMPLE 13

1-(4-Methoxyphenethyl)-4-(2-phenoxyethyl)piperidine

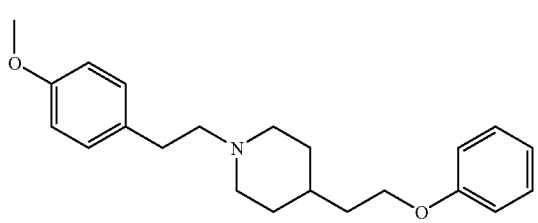

$^1$H NMR (400 MHz, DMSO-d$_6$): δ 1.40-1.90 (m, 9H), 2.70-3.10 (m, 6H), 3.70 (s, 3H), 3.98 (m, 2H), 6.84 (d, 2H), 6.90 (d, 3H), 7.13 (t, 2H), 7.23 (m, 2H).
m/z 340 [M+1]$^+$.

EXAMPLE 14

1-Phenethyl-4-(2-phenoxyethyl)piperidine

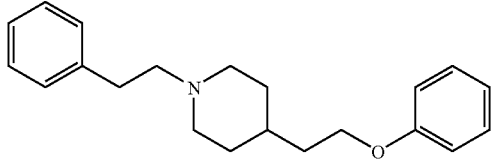

$^1$H NMR (400 MHz, DMSO-d$_6$): δ 1.5-1.9 (m, 9H), 2.8-3.1 (m, 6H), 4.01 (m, 2H), 6.91 (m, 3H), 7.2-7.3 (m, 7H).
m/z 310 [M+1]$^+$.

EXAMPLE 15

1-(3-(Trifluoromethyl)phenethyl)-4-(2-phenoxyethyl)piperidine

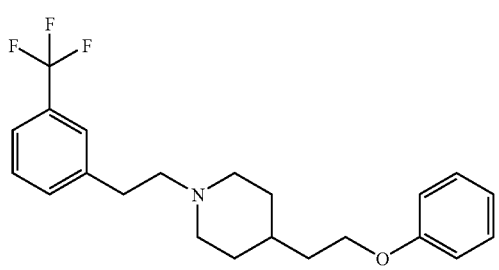

$^1$H NMR (400 MHz, CDCl$_3$): δ 1.4-1.9 (m, 8H), 2.6-3.7 (m, 7H), 3.97 (m, 2H), 6.90 (m, 3H), 7.24 (m, 2H), 7.51-7.61 (m, 4H).
m/z 378 [M+1]$^+$.

EXAMPLE 16

1-(4-(Trifluoromethyl)phenethyl)-4-(2-phenoxyethyl)piperidine

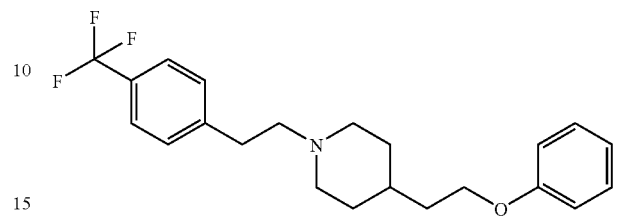

$^1$H NMR (400 MHz, DMSO-d$_6$): δ 1.4-1.7 (m, 8H), 2.6-3.1 (m, 7H), 3.97 (m, 2H), 6.90 (m, 3H), 7.25 (m, 2H), 7.47 (t, 2H), 7.64 (t, 2H).
m/z 378 [M+1]$^+$.

EXAMPLE 17

1-(2-(Trifluoromethyl)phenethyl)-4-(2-phenoxyethyl)piperidine

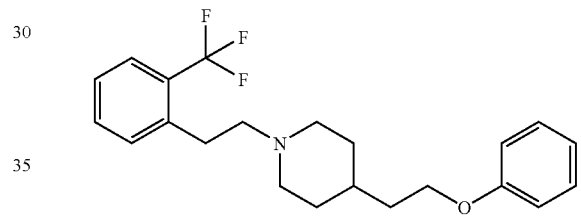

$^1$H NMR (400 MHz, CDCl$_3$): δ 1.4-1.7 (m, 8H), 2.7-3.2 (m, 7H), 3.97 (t, 2H), 6.91 (m, 3H), 7.25 (m, 2H), 7.44 (t, 1H), 7.49 (d, 1H), 7.63 (t, 1H), 7.68 (d, 1H).
m/z 378 [M+1]$^+$.

The following compounds can be prepared using the same procedures as for Example 11:

1-[2-(2-Fluoro-3,4-dimethoxyphenyl)ethyl]-4-(2-phenoxyethyl)piperidine
4-(2-Phenoxyethyl)-1-[2-(2,3,4-trimethoxyphenyl)ethyl]piperidine
1-[2-(2-Fluorophenyl)ethyl]-4-(2-phenoxyethyl)piperidine
1-[2-(3-Fluorophenyl)ethyl]-4-(2-phenoxyethyl)piperidine
1-[2-(4-Fluorophenyl)ethyl]-4-(2-phenoxyethyl)piperidine
1-[2-(3,4-Difluorophenyl)ethyl]-4-(2-phenoxyethyl)piperidine
4-(2-Phenoxyethyl)-1-(2-m-tolylethyl)piperidine
1-[2-(3-Chlorophenyl)ethyl]-4-(2-phenoxyethyl)piperidine
1-[2-(4-Chloro-3-methoxyphenyl)ethyl]-4-(2-phenoxyethyl)piperidine
4-(2-Phenoxyethyl)-1-[2-(4-trifluoromethoxyphenyl)ethyl]piperidine
4-[2-(4-Fluorophenoxy)ethyl]-1-[2-(4-methoxyphenyl)ethyl]piperidine
4-[2-(4-Fluorophenoxy)ethyl]-1-[2-(4-trifluoromethoxyphenyl)ethyl]piperidine
4-[2-(2-Fluorophenoxy)ethyl]-1-[2-(4-methoxyphenyl)ethyl]piperidine
4-[2-(2-Fluorophenoxy)ethyl]-1-[2-(4-trifluoromethoxyphenyl)ethyl]piperidine 1-(2-Benzo[1,3]dioxol-5-ylethyl)-4-[2-(4-fluorophenoxy) ethyl]piperidine and
1-(2-Benzo[1,3]dioxol-5-ylethyl)-4-[2-(2-fluorophenoxy) ethyl]piperidine.

EXAMPLE 18

1-(3,4-Dimethoxyphenethyl)-4-(2-phenoxyethyl) piperazine dihydrochloride

Step 1: 2-[(2-Hydroxy-ethyl)-(2-phenoxy-ethyl)-amino]ethanol (H)

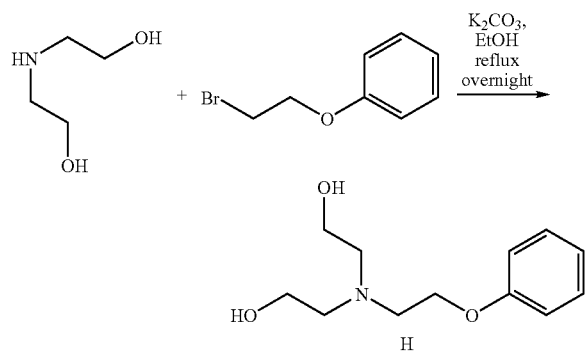

The reaction mixture of 2-(2-hydroxy-ethylamino)ethanol (32 g, 310 mmol), 1-(2-bromoethoxy)benzene (51 g, 256 mmol), and potassium carbonate (70 g, 512 mmol) in ethanol (200 mL) was refluxed overnight, concentrated, and partitioned between water and ethyl acetate. The organic layer was washed with brine, dried over anhydrous sodium sulfate, and concentrated. The residue was purified by column chromatography to afford the title compound (45 g, 78%).

Step 2: Bis-(2-chloroethyl)-(2-phenoxyethyl)amine hydrochloride (I)

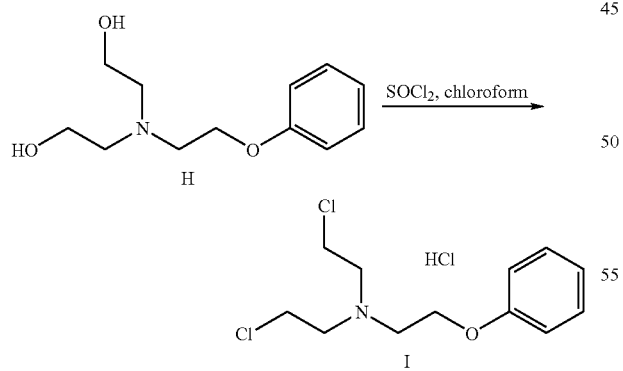

To an ice-cold solution of 2-[(2-hydroxyethyl)-(2-phenoxyethyl)-amino]ethanol (H, 43.9 g, 194 mmol) in chloroform (140 mL) was added thionyl chloride (SOCl$_2$; 114.8 g, 965 mmol) dropwise. The reaction mixture was then reflux for 1.5 h and concentrated. The residue was then suspended in the mixture of ethyl acetate and isopropyl ether. The precipitate was filtered and dried in a vacuum oven to afford the title compound quantitatively as a light brown crystal. This product was then used without further purification.

Step 3: 1-(3,4-Dimethoxyphenethyl)-4-(2-phenoxy-ethyl)piperazine dihydrochloride

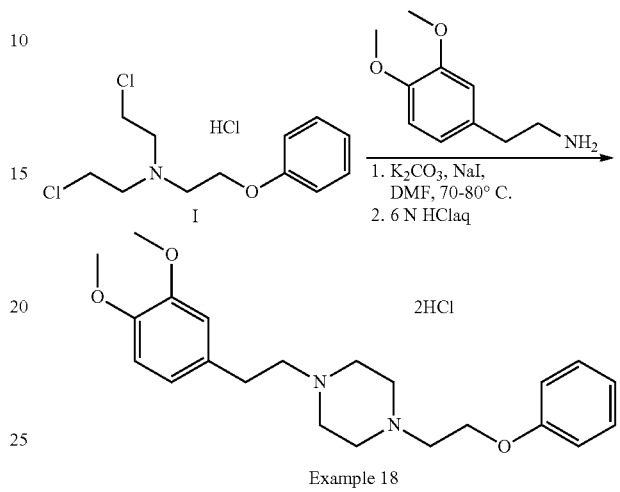

Example 18

The reaction mixture of bis-(2-chloroethyl)-(2-phenoxyethyl)amine (0.895 g, 3 mmol), 2-(3,4-dimethoxyphenyl) ethylamine (0.548 g, 3 mmol), potassium carbonate (K$_2$CO$_3$; 1.277 g, 9 mmol), and sodium iodide (NaI; 0.899 g, 6 mmol) in DMF (6 mL) was stirred at 70-80° C. for 5 h, quenched with water, and extracted with ethyl acetate. The organic layer was dried over anhydrous sodium sulfate and concentrated. The residue was suspended in 6 N HClaq (pH=3-4) and filtered. The filter cake was then washed with ethyl acetate and ethanol and dried to afford the title compound as a pale white solid (330 mg, 23%).

$^1$H NMR (400 MHz, CD$_3$OD): δ 3.08 (m, 2H), 3.50 (m, 2H), 3.74-3.84 (m, 16H), 4.44 (t, 2H), 6.85-7.05 (m, 6H), 7.32 (m, 2H).

m/z 371 [M−2HCl+1]$^+$.

The following compounds were prepared using the same method as described in Example 18.

EXAMPLE 19

1-(2-Methoxyphenethyl)-4-(2-phenoxyethyl)piperazine dihydrochloride

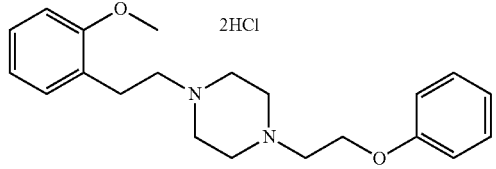

$^1$H NMR (400 MHz, CD$_3$OD): δ 3.13 (m, 2H), 3.46 (m, 2H), 3.5-3.9 (m, 13H), 4.45 (t, 2H), 6.90-7.06 (m, 5H), 7.24-7.35 (m, 4H).

m/z 341 [M−2HCl+1]$^+$.

EXAMPLE 20

1-(3-Methoxyphenethyl)-4-(2-phenoxyethyl)piperazine dihydrochloride

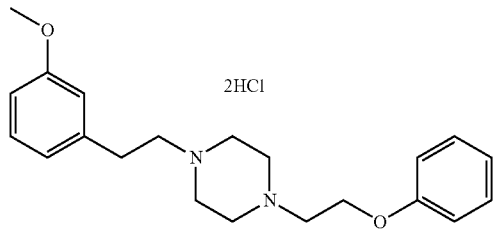

¹H NMR (400 MHz, CD₃OD): δ 3.12 (m, 2H), 3.52 (m, 2H), 3.65-3.95 (m, 13), 4.44 (t, 2H), 6.83-6.91 (m, 3H), 7.01-7.05 (m, 3H), 7.23-7.35 (m, 3H).

m/z 341 [M−2HCl+1]⁺.

EXAMPLE 21

1-(4-Methoxyphenethyl)-4-(2-phenoxyethyl)piperazine dihydrochloride

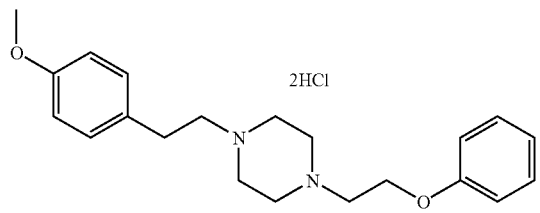

¹H NMR (400 MHz, CD₃OD): δ 3.08 (m, 2H), 3.48 (m, 2H), 3.6-3.0 (m, 13H), 4.45 (t, 2H), 6.90 (m, 2H), 7.03 (m, 3H), 7.23 (m, 2H), 7.32 (m, 2H).

m/z 341 [M−2HCl+1]⁺.

EXAMPLE 22

1-(2-(Benzo[d][1,3]dioxol-5-yl)ethyl)-4-(2-phenoxyethyl)piperazine dihydrochloride

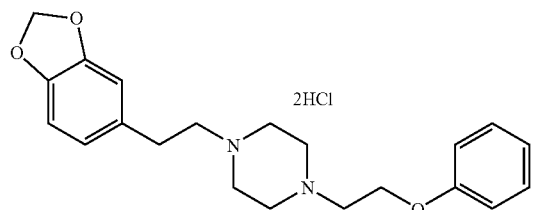

¹H NMR (400 MHz, CD₃OD): δ 3.05 (m, 2H), 3.46 (m, 2H), 3.6-3.9 (m, 10H), 4.42 (t, 2H), 5.93 (s, 2H), 6.38 (s, 2H), 6.84 (s, 1H), 7.01-7.04 (m, 3H), 7.32 (dd, 2H).

m/z 355 [M−2HCl+1]⁺.

EXAMPLE 23

1-(2-Fluorophenethyl)-4-(2-phenoxyethyl)piperazine dihydrochloride

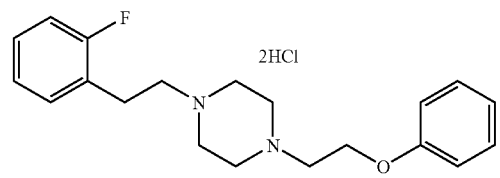

¹H NMR (400 MHz, CD₃OD): δ 3.21 (m, 2H), 3.50 (m, 2H), 3.6-3.9 (m, 10H), 4.39 (m, 2H), 6.98-7.21 (m, 5H), 7.30-7.40 (m, 4H).

m/z 329 [M−2HCl+1]⁺.

EXAMPLE 24

1-(3,4-Difluorophenethyl)-4-(2-phenoxyethyl)piperazine dihydrochloride

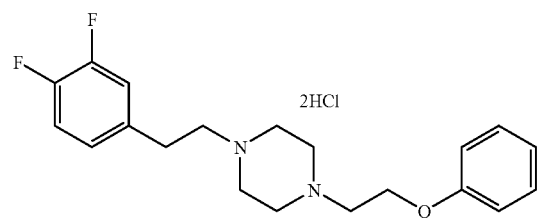

¹H NMR (400 MHz, CD₃OD): δ 3.14 (m, 2H), 3.51 9 m, 2H), 3.6-3.9 (m, 10H), 4.43 (t, 2H), 6.98-7.05 (m, 3H), 7.06-7.35 (m, 5H).

m/z 347 [M−2HCl+1]⁺.

EXAMPLE 25

1-(3-(Trifluoromethyl)phenethyl)-4-(2-phenoxyethyl)piperazine dihydrochloride

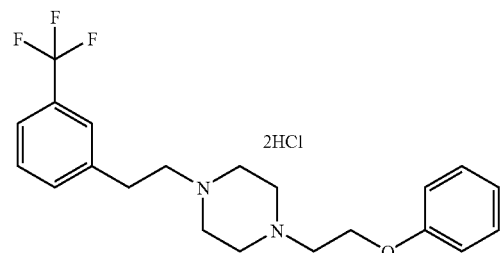

¹H NMR (400 MHz, CD₃OD): δ 3.25 (m, 2H), 3.54 (m, 2H), 3.7-3.9 (m, 10H), 4.45 (m, 2H), 7.02 (m, 3H), 7.34 (m, 2H), 7.55-7.69 (m, 4H).

m/z 379 [M−2HCl+1]⁺.

EXAMPLE 26

1-(2-(Trifluoromethoxy)phenethyl)-4-(2-phenoxy-ethyl)piperazine dihydrochloride

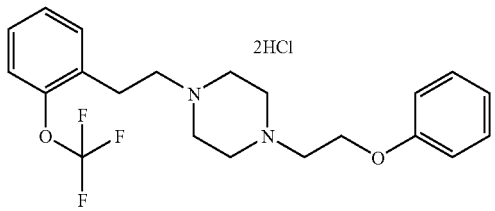

$^1$H NMR (400 MHz, CD$_3$OD+CDCl$_3$): δ 3.22 (m, 2H), 3.42 (m, 2H), 3.6-3.8 (m, 10H), 4.43 (t, 2H), 6.99 (m, 3H), 7.27-7.39 (m, 5H), 7.47 (d, 1H).

m/z 395 [M−2HCl+1]$^+$.

EXAMPLE 27

1-Phenethyl-4-(2-phenoxyethyl)piperazine dihydrochloride

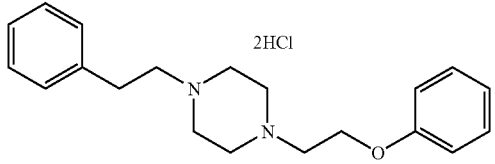

$^1$H NMR (400 MHz, CD$_3$OD+CDCl$_3$): δ 3.15 (m, 2H), 3.48 (m, 2H), 3.7-4.0 (m, 10H), 4.43 (t, 2H), 6.99 (m, 3H), 7.25-7.34 (m, 7H).

m/z 311 [M−2HCl+1]$^+$.

The following compounds can be prepared using the same procedure as described in Example 18:

1-[2-(2-Fluoro-3,4-dimethoxyphenyl)ethyl]-4-(2-phenoxy-ethyl)piperazine
1-(2-Phenoxyethyl)-4-[2-(2,3,4-trimethoxyphenyl)ethyl]piperazine
1-[2-(3-Fluorophenyl)ethyl]-4-(2-phenoxyethyl)piperazine
1-[2-(4-Fluorophenyl)-ethyl]-4-(2-phenoxyethyl)piperazine
1-(2-Phenoxyethyl)-4-(2-m-tolylethyl)piperazine
1-(2-Phenoxyethyl)-4-[2-(2-trifluoromethyl-phenyl)ethyl]piperazine
1-(2-Phenoxyethyl)-4-[2-(4-trifluoromethylphenyl)ethyl]piperazine
1-(2-Phenoxyethyl)-4-[2-(3-trifluoromethoxyphenyl)ethyl]piperazine
1-[2-(3-Chloro-phenyl)ethyl]-4-(2-phenoxyethyl)piperazine and
1-[2-(3-Chloro-4-methoxyphenyl)ethyl]-4-(2-phenoxy-ethyl)piperazine.

EXAMPLE 28

1-(3,4-Dimethoxyphenethyl)-4-(2-(4-chlorophenoxy)ethyl)piperazine dihydrochloride

Step 1: 2-(4-Chlorophenoxy)ethyl 4-methylbenzenesulfonate (J)

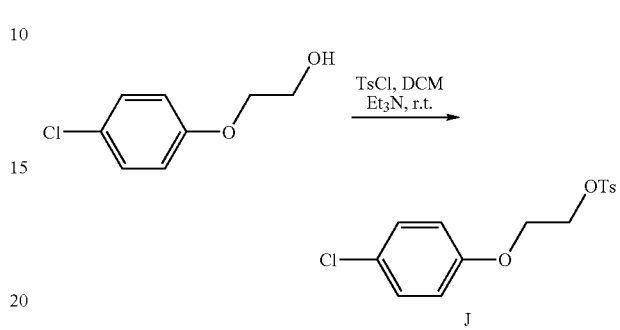

To a solution of 2-(4-chlorophenoxy)ethanol (2.0 g, 11.6 mmol) in DCM (10 mL) was added Et$_3$N (5 mL) and 4-methylbenzene-1-sulfonyl chloride (TsCl; 2.43 g, 12.8 mmol) sequentially. The reaction mixture was stirred at room temperature overnight and partitioned between water and ethyl acetate. The organic layer was washed with water, 5% sodium bicarbonate (NaHCO$_3$), and brine and concentrated. The resulting residue was washed with hexane to afford the title compound quantitatively.

Step 2: 1-(3,4-Dimethoxyphenethyl)piperazine dihydrochloride (L)

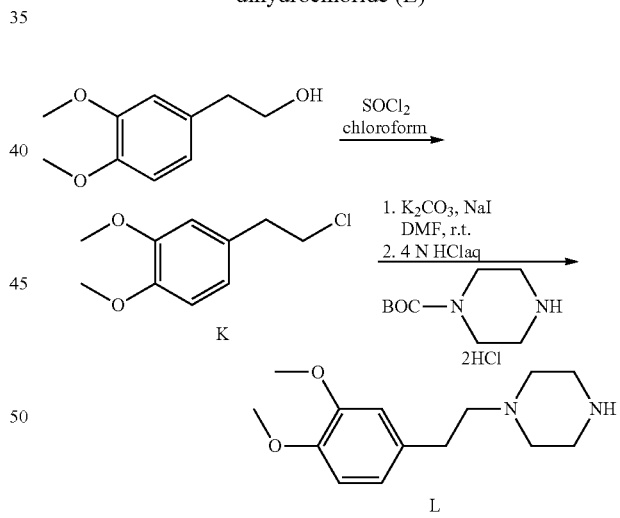

The reaction mixture of 2-(3,4-dimethoxyphenyl)ethanol (6.0 g, 32.8 mmol) and thionyl chloride (19 g, 164 mmol) in chloroform (20 mL) was stirred at reflux for 4 h, concentrated, and partitioned between water and ethyl acetate. The organic layer was washed with NaHCO$_3$ and brine, dried over anhydrous sodium sulfate, and concentrated to afford 4-(2-chloroethyl)-1,2-dimethoxybenzene (K) quantitatively (6.6 g).

A reaction mixture of 4-(2-chloroethyl)-1,2-dimethoxybenzene (3.6 g, 17.9 mmol), piperazine-1-carboxylic acid t-butyl ester (4.0 g, 21.5 mmol), K$_2$CO$_3$ (4.97 g, 36 mmol), and NaI (2.7 g, 18 mmol) in DMF (20 mL) was stirred at 80° C. for 3 h, cooled to room temperature, and partitioned between water and ethyl acetate. The organic layer was washed with water and brine, dried over anhydrous sodium sulfate, and concentrated. The residue was purified by column chromatography to afford 4-[2-(3,4-dimethoxy-phenyl)-ethyl]-piperazine-1-carboxylic acid t-butyl ester (4.8 g, 76%) which was dissolved in 4 N HCl in dioxane. This solution was stirred at room temperature for 4 h, concentrated, and dried in a high vacuum oven to give the title compound quantitatively.

Step 3: 1-(3,4-Dimethoxyphenethyl)-4-(2-(4-chlorophenoxy)ethyl)piperazine dihydrochloride

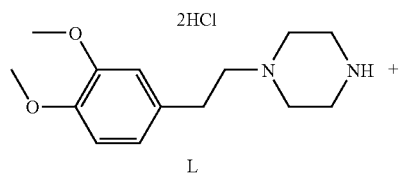

L

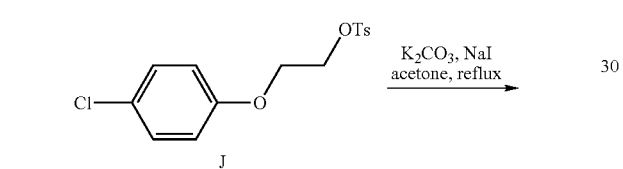

J

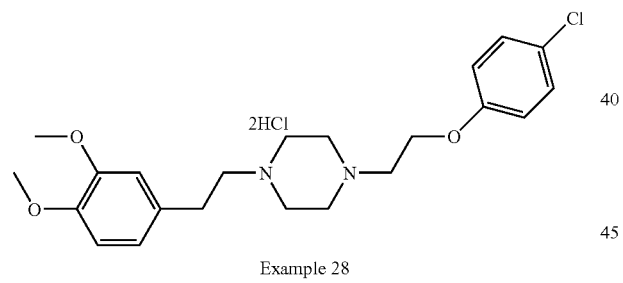

Example 28

To the solution of 1-(3,4-dimethoxyphenethyl)piperazine dihydrochloride (502 mg, 1.55 mmol) and 2-(4-chlorophenoxy)ethyl 4-methylbenzenesulfonate (460 mg, 1.4 mmol) in acetone (20 mL) was added NaI (465 mg, 3.1 mmol) and K$_2$CO$_3$ (1.1 g, 7.0 mmol). The reaction mixture was then refluxed overnight and concentrated. The residue was partitioned between ethyl acetate and water. The organic layer was washed with water and brine, dried over anhydrous sodium sulfate, and concentrated. The resulting residue was purified by column chromatography to afford 1-(3,4-dimethoxyphenethyl)-4-(2-(4-chlorophenoxy)ethyl)piperazine which was suspended in 6 N HClaq. (pH=3). The precipitate was filtered, washed with cold ethanol, and dried to afford the title compound (350 mg, 52%).

$^1$H NMR (400 MHz, DMSO-d$_6$): δ 2.96 (m, 2H), 3.4 (m, 12H), 3.70 (s, 3H), 3.74 (s, 3H), 4.36 (b, 2H), 6.76 (d, 1H), 6.89 (m, 2H), 7.03 (m, 2H), 7.34 (m, 2H).

m/z 405 [M−2HCl+1]$^+$.

EXAMPLE 29

1-(2-(2-Chlorophenoxy)ethyl)-4-(3,4-dimethoxyphenethyl)piperazine dihydrochloride

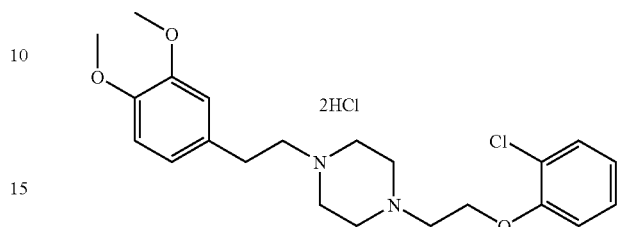

The title compound was prepared using the same procedure as described in Example 28 by replacing 2-(4-chlorophenoxy)ethyl 4-methylbenzenesulfonate with 2-(2-chlorophenoxy)ethyl 4-methylbenzenesulfonate in Step 1.

$^1$H NMR (400 MHz, DMSO-d$_6$): δ 2.96 (b, 2H), 3.4 (m, 12H), 3.70 (s, 3H), 3.72 (s, 3H), 4.44 (b, 2H), 6.76 (d, 1H), 6.89 (m, 2H), 6.98 (m, 1H), 7.20 (d, 1H), 7.33 (m, 1H), 7.46 (d, 1H).

m/z 405 [M−2HCl+1]$^+$.

EXAMPLE 30

4-(2-(4-(3,4-Dimethoxyphenethyl)piperazin-1-yl)ethyloxy)benzonitrile dihydrochloride Step 1: 4-(2-Bromoethoxy)benzonitrile (M)

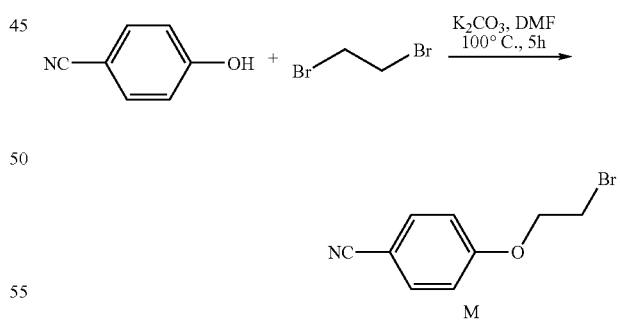

A reaction mixture of 4-hydroxybenzonitrile (1.19 g, 10 mmol), 1,2-dibromoethane (9.39 g, 50 mmol), and K$_2$CO$_3$ (4.14 g, 30 mmol) in DMF (20 mL) was stirred at 100° C. for 5 h and cooled to room temperature. To the reaction mixture was added ethyl acetate and water. The organic layer was washed with brine, dried over anhydrous sodium sulfate, and concentrated. The residue was purified by column chromatography to afford the 4-(2-bromoethoxy)benzonitrile (1.2 g, 53%).

Step 2: 4-(2-(4-(3,4-Dimethoxyphenethyl)piperazin-1-yl)ethyloxy)benzonitrile dihydrochloride

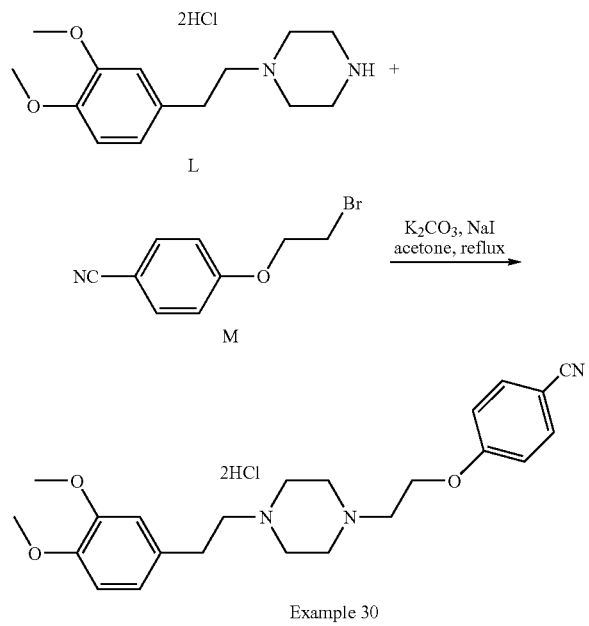

The title compound was prepared (41% yield) using the same procedures as described in Example 28 (Step 3) by replacing 2-(4-chlorophenoxy)ethyl 4-methylbenzenesulfonate with 4-(2-bromoethoxy)benzonitrile.

$^1$H NMR (400 MHz, DMSO-$d_6$): δ 2.95-3.00 (m, 3H), 3.20-3.60 (m, 11H), 3.70 (s, 3H), 7.73 (s, 3H), 4.46 (b, 2H), 6.77 (d, 1H), 6.88 (d, 2H), 7.17 (d, 2H), 7.79 (d, 2H).

m/z 396 [M−2HCl+1]$^+$.

The following compounds were prepared using the same procedure as described in Example 30 by replacing 4-hydroxybenzonitrile with the corresponding substituted phenol.

EXAMPLE 31

1-(3,4-Dimethoxyphenethyl)-4-(2-(4-isopropylphenoxy)ethyl)piperazine dihydrochloride

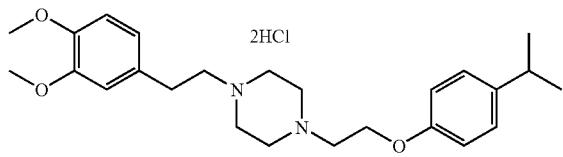

$^1$H NMR (400 MHz, CD$_3$OD): δ 1.20 (d, 6H), 2.69 (s, 1H), 2.85 (m, 1H), 3.09 (m, 2H), 3.51 (m, 2H), 3.73-3.80 (m, 15H), 4.14 (m, 2H), 6.85-6.97 (m, 5H), 7.18 (q, 2H).

m/z 413 [M−2HCl+1]$^+$.

EXAMPLE 32

1-(2-(2-(Trifluoromethyl)phenoxy)ethyl)-4-(3,4-dimethoxyphenethyl)piperazine dihydrochloride

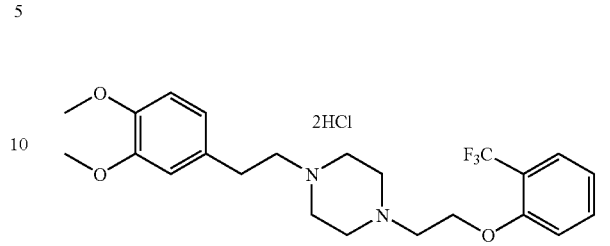

$^1$H NMR (400 MHz, CD$_3$OD): δ 3.09 (m, 2H), 3.51 (m, 2H), 3.6-4.0 (m, 16H), 4.62 (t, 2H), 6.85-6.96 (m, 3H), 7.16 (t, 1H), 7.26 (d, 1H), 7.63 (m, 2H).

m/z 439 [M−2HCl+1]$^+$.

The following compounds can be prepared using the same procedure as described Example 28 and 30:
- 1-[2-(3,4-Dimethoxyphenyl)ethyl]-4-[2-(4-fluoro-phenoxy)ethyl]piperazine
- 1-[2-(3,4-Dimethoxyphenyl)ethyl]-4-[2-(4-methoxyphenoxy)ethyl]piperazine
- 1-[2-(Biphenyl-4-yloxy)ethyl]-4-[2-(3,4-dimethoxyphenyl)ethyl]piperazine
- 1-[2-(Benzo[1,3]dioxol-5-yloxy)ethyl]-4-[2-(3,4-dimethoxyphenyl)ethyl]piperazine
- 1-[2-(3,4-Dimethoxy-phenyl)ethyl]-4-[2-(4-trifluoromethyl-phenoxy)ethyl]piperazine
- 1-[2-(3,4-Dimethoxy-phenyl)ethyl]-4-(2-p-tolyloxyethyl)piperazine
- 1-[2-(3,4-Dimethoxy-phenyl)ethyl]-4-[2-(4-imidazol-1-ylphenoxy)ethyl]piperazine
- 1-[2-(3,4-Dimethoxy-phenyl)ethyl]-4-[2-(4-trifluoromethoxyphenoxy)ethyl]piperazine
- 1-[2-(3,4-Dimethoxy-phenyl)ethyl]-4-[2-(2-fluorophenoxy)ethyl]piperazine
- 1-[2-(3,4-Dimethoxy-phenyl)ethyl]-4-[2-(2-methoxyphenoxy)ethyl]piperazine
- 1-[2-(3,4-Dimethoxy-phenyl)ethyl]-4-[2-(2-trifluoromethoxyphenoxy)ethyl]piperazine
- 1-[2-(3,4-Dimethoxy-phenyl)ethyl]-4-[2-(2-fluoro-4-methoxyphenoxy)ethyl]piperazine
- 1-[2-(3,4-Dimethoxy-phenyl)ethyl]-4-[2-(3-fluoro-4-methoxyphenoxy)ethyl]piperazine
- 1-[2-(3-Chloro-4-methoxy-phenoxy)ethyl]-4-[2-(3,4-dimethoxyphenyl)ethyl]piperazine
- 1-[2-(3,4-Dichloro-phenoxy)ethyl]-4-[2-(3,4-dimethoxyphenyl)ethyl]piperazine
- 1-[2-(4-Isopropoxy-phenyl)ethyl]-4-(2-phenoxy-ethyl)piperazine
- 1-[2-(4-Fluoro-phenoxy)ethyl]-4-[2-(4-isopropoxy-phenyl)ethyl]piperazine
- 1-[2-(2-Fluoro-phenoxy)ethyl]-4-[2-(4-isopropoxy-phenyl)ethyl]piperazine
- 1-[2-(2-Fluoro-phenoxy)ethyl]-4-[2-(3,4,5-trimethoxy-phenyl)ethyl]piperazine
- 1-[2-(2-Fluoro-phenoxy)ethyl]-4-[2-(4-methoxy-phenyl)ethyl]piperazine
- 1-[2-(4-Fluoro-phenoxy)ethyl]-4-[2-(4-methoxy-phenyl)ethyl]piperazine
- 1-(2-Benzo[1,3]dioxol-5-ylethyl)-4-[2-(4-fluoro-phenoxy)ethyl]piperazine
- 1-(2-Phenoxyethyl)-4-[2-(4-trifluoromethoxyphenyl)ethyl]piperazine 4-(2-{4-[2-(4-Trifluoromethoxyphenyl)ethyl]piperazin-1-yl}ethoxy)benzonitrile
1-[2-(4-Fluoro-phenoxy)ethyl]-4-[2-(4-trifluoromethoxyphenyl)ethyl]piperazine
1-[3-(3,4-Dimethoxy-phenyl)propyl]-4-(2-phenoxyethyl)piperazine
1-[3-(3,4-Dimethoxy-phenyl)propyl]-4-[2-(4-fluorophenoxy)ethyl]piperazine
1-(3-Benzo[1,3]dioxol-5-ylpropyl)-4-(2-phenoxyethyl)piperazine
1-(3-Benzo[1,3]dioxol-5-ylpropyl)-4-[2-(4-fluorophenoxy)ethyl]piperazine
1-[2-(4-Fluoro-phenoxy)ethyl]-4-[3-(4-methoxyphenyl)propyl]piperazine
1-[2-(4-Fluoro-phenoxy)ethyl]-4-[3-(4-isopropoxyphenyl)propyl]piperazine
1-[2-(4-Fluoro-phenoxy)ethyl]-4-[3-(4-trifluoromethoxyphenyl)propyl]piperazine
1-[2-(4-Fluoro-phenoxy)ethyl]-4-[3-(3,4,5-trimethoxyphenyl)propyl]piperazine and
1-[2-(4-t-Butyl-phenoxy)ethyl]-4-[2-(3,4-dimethoxyphenyl)ethyl]piperazine.

The invention claimed is:
1. A compound of general formula (I)

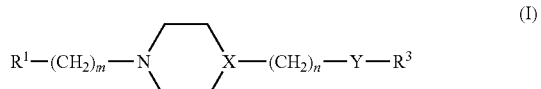

in which:
R¹ represents a phenyl group that is substituted by one, two or three substituents selected from the group consisting of (1-2C)alkylenedioxy, a halogen atom, a hydroxyl group, a cyano group, a (1-4C) alkyl group, a (3-6C) cycloalkyl group, a halo(1-4C) alkyl group, a (1-4C) alkoxy group, and a halo(1-4C)alkoxy group;
m is 2, 3, 4, or 5;
X is CH or N;
n is 1, 2, 3, 4 or 5, provided that when X is N, n is 2, 3, 4 or 5;
Y is O or NR² or S;
R² is hydrogen, (1-4C)alkyl or phenyl(1-4C)alkyl, or is as defined for R³; and
R³ represents indan-1-yl, indan-2-yl, 1,2,3,4-tetrahydronaphth-1-yl, or 1,2,3,4-tetrahydronaphth-2-yl, each of which may bear a hydroxyl substituent on a non-aromatic carbon atom; a (3-6C) cycloalkyl group; or a phenyl group that is unsubstituted or substituted by one, two, or three substituents selected from the group consisting of (1-2C)alkylenedioxy, a halogen atom, a hydroxyl group, a (1-4C) alkyl group, a (3-6C)cycloalkyl group, a cyano group; a phenyl group, an imidazolyl group, a halo(1-4C) alkyl group, a (1-4C)alkoxy group, and a halo(1-4C)alkoxy group;
or a pharmaceutically acceptable salt thereof.
2. A compound as recited in claim 1, in which R¹ represents benzo[1,3]dioxol-5-yl, 2-fluorophenyl, 3-fluorophenyl, 4-fluorophenyl, 3,4-difluorophenyl, 3-chlorophenyl, 3-methylphenyl, 2-trifluoromethylphenyl, 3-trifluoromethylphenyl, 4-trifluoromethylphenyl, 2-methoxyphenyl, 3-methoxyphenyl, 4-methoxyphenyl, 4-isopropoxyphenyl, 3,4-dimethoxyphenyl, 2,3,4-trimethoxyphenyl, 3,4,5-trimethoxyphenyl, 2-fluoro-3,4-dimethoxyphenyl, 3-chloro-4-methoxyphenyl, 4-chloro-3-methoxyphenyl, 2-trifluoromethoxyphenyl, 4-trifluoromethoxyphenyl, or 3-trifluoromethoxyphenyl.
3. A compound as recited in claim 1, in which R¹ represents benzo[1,3]dioxol-5-yl, 2-fluorophenyl, 3,4-difluorophenyl, 2-trifluoromethylphenyl, 3-trifluoromethylphenyl, 4-trifluoromethylphenyl, 2-methoxyphenyl, 3-methoxyphenyl, 4-methoxyphenyl, 3,4-dimethoxyphenyl or 2-trifluoromethoxyphenyl.
4. A compound as recited in claim 1, in which R¹ represents 3,4-dimethoxyphenyl, 3,4,5-trimethoxyphenyl, 4-methoxyphenyl, 4-isopropoxyphenyl, or 4-trifluoromethoxyphenyl.
5. A compound as recited in any of claims 1 to 4, in which either m or n is 2, or both m and n are 2.
6. A compound as recited in any of claims 1 to 4, in which Y is O or NH.
7. A compound as recited in claim 5, in which Y is O or NH.
8. A compound as recited in claims 1 to 4, in which R³ represents phenyl, benzo[1,3]dioxol-5-yl, 2-fluorophenyl, 4-fluorophenyl, 2,4-difluorophenyl, 4-trifluoromethoxyphenyl, 2-chlorophenyl, 4-chlorophenyl, 3,4-dichlorophenyl, 4-methylphenyl, 4-isopropylphenyl, 4-t-butylphenyl, 4-cyanophenyl, 2-trifluoromethylphenyl, 4-trifluoromethylphenyl, 2-methoxyphenyl, 4-methoxyphenyl, 4-biphenyl, 4-(1-imidazolyl)phenyl, 2-fluoro-4-methoxyphenyl, 3-fluoro-4-methoxyphenyl, 3-chloro-4-methoxyphenyl, 2-trifluoromethoxyphenyl or 4-trifluoromethoxyphenyl.
9. A compound as recited in claim 8, in which either m or n is 2, or both m and n are 2.
10. A compound as recited in claim 8, in which Y is O or NH.
11. A compound as recited in claim 9, in which Y is O or NH.
12. A compound as recited in any one of claims 1 to 4, in which R³ represents phenyl, 2-fluorophenyl, 4-fluorophenyl, 2-chlorophenyl, 4-chlorophenyl, 4-methylphenyl, 4-isopropylphenyl, 4-cyanophenyl or 2-trifluoromethylphenyl.
13. A compound as recited in claim 12, in which either morn is 2, or both m and n are 2.
14. A compound as recited in claim 12, in which Y is O or NH.
15. A compound as recited in claim 13, in which Y is O or NH.
16. A compound as claimed in any one of claims 1 to 4, in which R³ represents a 4-fluorophenyl group.
17. A compound as recited in claim 16, in which either m or n is 2, or both m and n are 2.
18. A compound as recited in claim 16, in which Y is O or NH.
19. A compound as recited in claim 17, in which Y is O or NH.
20. A compound as recited in claim 1, which is selected from:
1-(3,4-Dimethoxyphenethyl)-4-(2-(4-fluorophenoxy)ethyl)piperidine;
1-(4-(Trifluoromethyl)phenethyl)-4-(2-phenoxyethyl)piperidine;
4-(2-(2-Fluorophenoxy)ethyl)-1-(3,4-dimethoxyphenethyl)piperidine;
1-(3,4-Dimethoxyphenethyl)-4-(2-phenoxyethyl)piperazine;
1-(3-Methoxyphenethyl)-4-(2-phenoxyethyl)piperazine;
1-(4-Methoxyphenethyl)-4-(2-phenoxyethyl)piperazine;
1-(2-(Benzo[d][1,3]dioxol-5-yl)ethyl)-4-(2-phenoxyethyl)piperazine;
1-(3,4-Difluorophenethyl)-4-(2-phenoxyethyl)piperazine;
1-(3,4-Dimethoxyphenethyl)-4-(2-(4-chlorophenoxy)ethyl)piperazine;

4-(2-(4-(3,4-Dimethoxyphenethyl)piperazin-1-yl)ethyloxy)benzonitrile;

and pharmaceutically acceptable salts thereof.

21. A process for preparing a compound as recited in claim 1, which comprises
a) reducing a compound of general formula (II)

with a reducing agent; or b) for a compound of formula (I) in which X is N, reacting a compound of general formula (III)

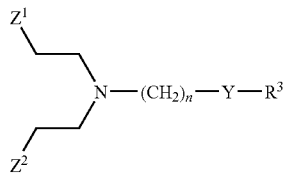

in which each of $Z^1$ and $Z^2$ independently represents a leaving atom or group, with a compound of general formula (IV)

R$^1$—(CH$_2$)$_m$—NH$_2$      (IV)

or a corresponding compound in which one or two substituents on R$^1$ are protected; or c) for a compound of formula (I) in which X is N, reacting a compound of general formula (V)

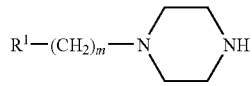

with a compound of general formula (VI)

Z$^3$—(CH$_2$)$_n$—Y—R$^3$      (VI)

in which $Z^3$ represents a leaving atom or group, and R$^1$, m, n, Y, and R$^3$ are previously defined in claim 1;

followed by removing any protecting group and, optionally, forming a pharmaceutically acceptable salt.

22. A compound of general formula (II)

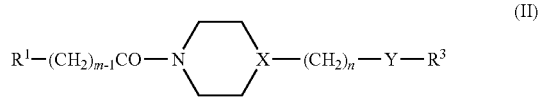

in which
R$^1$ represents a phenyl group that is substituted by one, two or three substituents selected from the group consisting of (1-2C)alkylenedioxy, a halogen atom, a hydroxyl group, a cyano group, a (1-4C) alkyl group, a (3-6C) cycloalkyl group, a halo(1-4C) alkyl group, a (1-4C) alkoxy group, and a halo(1-4C)alkoxy group;

m is 2, 3, 4, or 5;

X is CH or N;

n is 1, 2, 3, 4 or 5, provided that when X is N, n is 2, 3, 4 or 5;

Y is O, NR$^2$, or S;

R$^2$ is hydrogen, (1-4C)alkyl or phenyl(1-4C)alkyl, or is as defined for R$^3$; and R$^3$ represents indan-1-yl, indan-2-yl, 1,2,3,4-tetrahydronaphth-1-yl, or 1,2,3,4-tetrahydronaphth-2-yl, each of which may bear a hydroxyl substituent on a non-aromatic carbon atom; a (3-6C) cycloalkyl group; or a phenyl group that is unsubstituted or substituted by one, two, or three substituents selected from the group consisting of (1-2C)alkylenedioxy, a halogen atom, a hydroxyl group, a (1-4C) alkyl group, a (3-6C)cycloalkyl group, a cyano group; a phenyl group, an imidazolyl group, a halo(1-4C) alkyl group, a (1-4C)alkoxy group, and a halo(1-4C)alkoxy group;

or a pharmaceutically acceptable salt thereof.

23. A pharmaceutical composition, which comprises a compound as claimed in claim 1, and a pharmaceutically acceptable diluent or carrier.

24. A compound which is 1-[2-(4-Fluorophenoxy)ethyl]-4-[3-(4-trifluoromethoxyphenyl)propyl]piperazine, or a pharmaceutically acceptable salt thereof.

25. A pharmaceutical composition, which comprises a compound which is 1-[2-(4-Fluorophenoxy)ethyl]-4-[3-(4-trifluoromethoxyphenyl)propyl]piperazine, or a pharmaceutically acceptable salt thereof, and a pharmaceutically acceptable diluent or carrier.

* * * * *